United States Patent
Diwu et al.

(10) Patent No.: US 8,183,375 B2
(45) Date of Patent: *May 22, 2012

(54) DERIVATIVES OF 1,2-DIHYDRO-7-HYDROXYQUINOLINES CONTAINING FUSED RINGS

(75) Inventors: Zhenjun Diwu, Okemos, MI (US); Jixiang Liu, Eugene, OR (US); Kyle Gee, Springfield, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/901,713

(22) Filed: Oct. 11, 2010

(65) Prior Publication Data

US 2011/0027800 A1    Feb. 3, 2011

Related U.S. Application Data

(63) Continuation of application No. 11/560,579, filed on Nov. 16, 2006, now Pat. No. 7,816,519, which is a continuation of application No. 10/713,670, filed on Nov. 13, 2003, now Pat. No. 7,169,922, which is a continuation-in-part of application No. 09/922,333, filed on Aug. 4, 2001, now Pat. No. 6,716,979.

(60) Provisional application No. 60/223,086, filed on Aug. 4, 2000.

(51) Int. Cl.
  *C07D 471/04* (2006.01)
  *C07D 471/06* (2006.01)
  *G01N 1/30* (2006.01)
  *G01N 33/48* (2006.01)
  *G01N 33/50* (2006.01)

(52) U.S. Cl. ............ 546/36; 435/6.1; 435/40.5; 436/86; 436/92; 436/172; 436/800

(58) Field of Classification Search .................. None
See application file for complete search history.

(56) References Cited

U.S. PATENT DOCUMENTS

| | | |
|---|---|---|
| 3,336,293 A | 8/1967 | Cusic et al. |
| 4,544,546 A | 10/1985 | Wang et al. |
| 4,603,209 A | 7/1986 | Tsien et al. |
| 4,711,955 A | 12/1987 | Ward et al. |
| 4,849,362 A | 7/1989 | Demarinis et al. |
| 4,945,171 A | 7/1990 | Haugland et al. |
| 4,997,928 A | 3/1991 | Hobbs |
| 5,047,519 A | 9/1991 | Hobbs et al. |
| 5,049,673 A | 9/1991 | Tsien et al. |
| 5,137,810 A | 8/1992 | Sizemore et al. |
| 5,171,534 A | 12/1992 | Smith et al. |
| 5,208,148 A | 5/1993 | Haugland et al. |
| 5,227,487 A | 7/1993 | Haugland et al. |
| 5,290,706 A | 3/1994 | Camiener |
| 5,332,666 A | 7/1994 | Prober |
| 5,405,975 A | 4/1995 | Kuhn et al. |
| 5,453,517 A | 9/1995 | Kuhn et al. |
| 5,459,276 A | 10/1995 | Kuhn et al. |
| 5,501,980 A | 3/1996 | Katerinopoulos et al. |
| 5,516,911 A | 5/1996 | London et al. |
| 5,567,588 A | 10/1996 | Gold |
| 5,648,270 A | 7/1997 | Kuhn et al. |
| 5,696,157 A | 12/1997 | Wang et al. |
| 5,714,327 A | 2/1998 | Houthoff et al. |
| 5,750,409 A | 5/1998 | Herrmann et al. |
| 5,773,227 A | 6/1998 | Kuhn et al. |
| 5,847,162 A * | 12/1998 | Lee et al. ............... 549/227 |
| 5,936,087 A | 8/1999 | Benson et al. |
| 6,008,379 A | 12/1999 | Benson et al. |
| 6,080,852 A | 6/2000 | Lee et al. |
| 6,130,101 A | 10/2000 | Mao et al. |
| 6,140,500 A | 10/2000 | Yan et al. |
| 6,162,931 A | 12/2000 | Gee et al. |
| 6,191,278 B1 * | 2/2001 | Lee et al. ............... 546/41 |
| 6,372,907 B1 * | 4/2002 | Lee et al. ............... 546/41 |
| 6,399,392 B1 | 6/2002 | Haugland et al. |
| 6,713,622 B1 * | 3/2004 | Graham ............... 536/25.32 |
| 6,716,979 B2 * | 4/2004 | Diwu et al. ............... 544/99 |
| 7,169,922 B2 * | 1/2007 | Diwu et al. ............... 544/99 |
| 7,504,496 B2 | 3/2009 | Lee et al. |
| 7,550,570 B2 | 6/2009 | Lee et al. |
| 7,816,519 B2 * | 10/2010 | Diwu et al. ............... 544/99 |
| 2005/0112781 A1 * | 5/2005 | Lee et al. ............... 436/518 |

FOREIGN PATENT DOCUMENTS

| | | |
|---|---|---|
| EP | 0330444 | 8/1989 |
| SU | 926914 | 4/1992 |
| WO | WO 94/05688 | 3/1994 |

OTHER PUBLICATIONS

U.S. Appl. No. 09/922,333; Notice of Allowance mailed Aug. 1, 2003.
U.S. Appl. No. 09/922,333; Office Action mailed Feb. 26, 2003.
U.S. Appl. No. 09/922,333; Office Action mailed Nov. 25, 2002.
U.S. Appl. No. 09/922,333; Response to Feb. 26, 2003 Office Action filed May 22, 2003.
U.S. Appl. No. 09/922,333; Response to Nov. 25, 2002 Office Action filed Dec. 19, 2002.
U.S. Appl. No. 09/922,333; Response to Restriction Requirement filed Oct. 10, 2002.
U.S. Appl. No. 09/922,333; Restriction Requirement mailed Sep. 10, 2002.
U.S. Appl. No. 10/713,670; Notice of Allowance mailed Aug. 8, 2006.
U.S. Appl. No. 10/713,670; Office Action mailed Mar. 31, 2006.
U.S. Appl. No. 10/713,670; Office Action mailed Nov. 7, 2005.
U.S. Appl. No. 10/713,670; Response to Mar. 31, 2006 Office Action filed Jul. 28, 2006.

(Continued)

*Primary Examiner* — Fiona T Powers

(57) ABSTRACT

The present invention describes novel dyes, including coumarins, rhodamines, and rhodols that incorporate additional fused aromatic rings. The dyes of the invention absorb at a longer wavelength than structurally similar dyes that do not possess the fused aromatic rings. Many of the dyes of the invention are useful fluorescent dyes. The invention includes chemically reactive dyes, dye-conjugates, and the use of such dyes in staining samples and detecting ligands or other analytes.

13 Claims, 3 Drawing Sheets

OTHER PUBLICATIONS

U.S. Appl. No. 10/713,670; Response to Nov. 7, 2005 Office Action filed Jan. 27, 2006.
U.S. Appl. No. 10/713,670; Response to Restriction Requirement filed Aug. 24, 2005.
U.S. Appl. No. 10/713,670; Restriction Requirement mailed Aug. 19, 2005.
U.S. Appl. No. 11/560,579; Notice of Allowance mailed Jun. 10, 2010.
U.S. Appl. No. 11/560,579; Office Action mailed Jan. 25, 2010.
U.S. Appl. No. 11/560,579; Office Action mailed Apr. 21, 2008.
U.S. Appl. No. 11/560,579; Office Action mailed Jul. 18, 2007.
U.S. Appl. No. 11/560,579; Office Action mailed Sep. 18, 2008.
U.S. Appl. No. 11/560,579; Office Action mailed Jun. 11, 2009.
U.S. Appl. No. 11/560,579; Response to Apr. 21, 2008 Office Action filed Jun. 6, 2008.
U.S. Appl. No. 11/560,579; Response to Jun. 11, 2009 Office Action filed Nov. 12, 2009.
U.S. Appl. No. 11/560,579; Response to Jul. 18, 2007 Office Action filed Jan. 17, 2008.
U.S. Appl. No. 11/560,579; Response to Sep. 18, 2008 Office Action filed Mar. 17, 2009.
Amlaiky, Nourdine, et al., "A Novel RadioRodinated High Affinity Ligand for the D2 Dopamine Receptor", *Febs Letters*, vol. 176, No. 2, 1984; pp. 436-440.
Bouizar, Zhor, et al., "Purification and Characterization of Calcitonin Receptors in Rat Kidney Membranes by Covalent Cross-Linking Techniques.", *Eur. J. Biochem*, vol. 155, No. 1, 1986; pp. 141-147.
Brinkley, Michael, "A Brief Survey of Methods for Preparing Protein Conjugates with Dyes, Haptens, and Cross-Linking Reagents", *Bioconjugate Chemistry*, vol. 3, Issue 1, Jan.-Feb. 1992; pp. 2-13.
Browning, et al., "Studies on the Differing Effects of the Tumor Necrosis Factor and Lymphotoxin on the Growth of Several Human Tumor Lines", *Journal of Immunology*, vol. 143, Issue 6, 1989; pp. 1859-1867.
CA 2,417,816; Office Action mailed Aug. 16, 2006.
CA 2,417,816; Office Action mailed Sep. 28, 2007.
EP 01957438; International Search Report mailed Jul. 2, 2004.
EP 01957438; Examination Report mailed Feb. 23, 2005.
EP 01957438; Examination Report mailed Sep. 6, 2005.
EP 01957438; Examination Report mailed Nov. 28, 2005.
EP 08168939.0; European Search Report mailed on Mar. 26, 2009.
EP 08168939.0; Office Action mailed Jan. 28, 2010.
EP 08168939.0; EP Search Report mailed on May 28, 2009.
EP 08168939.0; Office Action mailed Apr. 14, 2011.
EP 10185403.2; Extended European Search Report mailed Apr. 18, 2011.
Furniss, Brian S., et al., "Resolution of Racemates", *Vogel's Textbook of Practical Organic Chemistry*, Fifth Ed, Longman Group UK Ltd., Essex 1989; pp. 809-823.
Gee, Kyle R., et al., "Novel Derivatization of Protein Thiols with Fluorinated Fluoresceins", *Tetrahedron Letters*, vol. 37, No. 44, 1996; pp. 7905-7908.
Hahn, Witold E., et al., "Cycloparaffins condensed with heterocyclic rings. V. Attempts at the synthesis of some 1,2,3,4-tetrahydro-and 1,2-benzo-3,4-dihydro-a-carboline", *Chemical Abstracts*, 66, Doc# 75925, 1967; p. 75925.
Haugland, Richard P., "Molecular Probes Handbook of Fluorescent Probes and Research Chemicals", *Chapters 1-3*, Molecular Probes, Inc, 1996, Sixth Edition 1996, Jul. 1980.
Haugland, Richard P., "Molecular Probes Handbook of Fluorescent Probes and Research Chemicals", *Ch 10: Enzymes, Enzyme Substrates and Enzyme Inhibitors* Sixth Edition, Molecular Probes, Inc. 1996; pp. 201-250.
Haugland, Rosaria P., et al., "Coupling of monoclonal antibodies with biotin", *Methods in Molecular Biology*, vol. 45, 1995, 223-233.
Haugland, Rosaria P., et al., "Coupling of monoclonal antibodies with enzymes", *Methods in Molecular Biology*, vol. 45, 1995; pp. 235-243.
Hougland, Rosaria P. "Coupling of monoclonal antibodies with fluorophores", *Methods in Molecular Biology*, vol. 45, Monoclonal Antibody Protocols 1995; pp. 205-221.
Heller, A., "Electrical Wiring of Redox Enzymes", *Acc. Chem. Res.*, vol. 23, No. 5, 1990; pp. 128-134.
Joshi, Saroj, et al., "ATP Synthase Complex from Bovine Heart Mitochondria", *J. Biol. Chem.*, vol. 265, No. 24, 1990; pp. 14518-14525.
Jung, Stephanie M., et al., "Crosslinking of platelet glycoprotein Ib by N-succinimidyl(4-azidophenyldithio)propionate and 3,3'-dithiobis(sulfosuccinimidyl propionate)", *Biochimia et Biophysica Acta*, vol. 761, Issue 2, 1983; pp. 152-162.
Kano, Shinzo, et al., "Formation of furo[3,2c]quinoline derivatives through the Fris-type acid catalyzed rearrangement of 1-arylazetidin-2-ones", *Heterocycles*, vol. 15, No. 2, Jan. 1, 1981; pp. 1011-1015.
Kendall, Debra A., et al., "A Fluorescence Assay to Monitor Vesicle Fusion and Lysis", *The Journal of Biological Chemistry*, vol. 257, No. 23, 1982; pp. 13892-13895.
Kidwai, Mazashir, et al., *Chemical Abstracts*, vol. 115, 1991; p. 29162.
Liu, J., et al., "Rational Design and Synthesis of a Novel Class of Highly Fluorescent Rhodamine Dyes that Have Strong Absorption at Long Wavelengths", *Tetrahedron Letters*, vol. 44, 2003; pp. 4355-4359.
Muller, Ralph, et al., "Efficient DNA sequencing with a Pulsed Semiconductor Laser and a New Fluorescent Dye Set", *Chemical Physics Letters*, vol. 279, Nov. 21, 1997; pp. 282-288.
Park, Linda S., et al., "Characterization of the Cell Surface Receptor for a Multi-Lineage Colony-Stimulating Factor (CSF-2alpha)*", *J. Biol. Chem.*, vol. 261, No. 1, 1986; pp. 205-210.
PCT International Search Report, WO 2002/012195 mailed Dec. 31, 2001.
Raju, B., et al., "A fluorescent indicator for measuring cytosolic free magnesium", *Am. J. Physiol.*, vol. 256, 1989; pp. C540-C548.
Razafimbelo, et al., "Chemical & Pharmaceutical Bulletin", vol. 46, No. 1, 1998; pp. 34-41.
Sandler, Stanley R., et al., "Organic Functional Group Preparations", vol. 3, New York: Academic Press, 1972; pp. 5-7.
Sauer, M., et al., "On-Line Diode Laser Based Time-Resolved Fluorescence Detection of Labeled Oligonucleotides in Capillary Gel Electrophoresis", *Biomedical Chromatography*, vol. 11, Issue 2, 1996; pp. 81-82.
Sauer, M., et al., "New Fluorescent Dyes in the Red region for Biodiagnostics", *Journal of Fluorescence*, vol. 5, No. 3, 1995; pp. 247-261.
Szoka, Francis J., et al., "Comparative Properties and Methods of Preparation of Lipid Vesicles (Liposomes)", *Annu. Rev. Biophys. Bioeng*, vol. 9, 1980; pp. 467-508.
Szoka, Francis, et al., "Procedure for Preparation of Liposomes with Large Internal Aqueous Space and High Capture by Reverse-Phase Evaporation.", *Proceedings of the National Academy of Sciences (PNAS)*, vol. 75, No. 9, Sep. 1978; pp. 4194-4198.
Temciuc, Ecaterina, et al., "An unexpected[2+2]-cycloaddition reaction of 4-methyldithieno-[3,4-b:3'2'-d]pyridinium iodide with dimethyl acetylenedicarboxylate", *Tetrahedron*, vol. 51, No. 48, 1995; pp. 13185-13196.
Tsien, R., et al., "Measurement of Cytosolic Free Ca 2+ With Quin2", *Methods in Enzymology*, vol. 172, 1989; pp. 230-244.
Von Blankenfeld, Gabriela, et al., "Derivatives of 1,2-dihydro-7-hydroxyquinolines containing fused rings", *Journal of Neuroscience Methods*, vol. 36, 1991; pp. 309-315.
Zarling, David A., et al., "Mapping of Lymphocyte Surface Polypeptide Antigens by Chemical Cross-Linking with BSOCOES", *Journal of Immunology*, vol. 124, No. 2, 1980; pp. 913-920.

* cited by examiner

DERIVATIVES OF 1,2-DIHYDRO-7-HYDROXYQUINOLINES CONTAINING FUSED RINGS

CROSS-REFERENCE TO RELATED APPLICATIONS

This application is a continuation of U.S. Ser. No. 11/560,579, filed Nov. 16, 2006, now U.S. Pat. No. 7,816,519, which is a continuation of U.S. Ser. No. 10/713,670, now U.S. Pat. No. 7,169,922, filed on Nov. 13, 2003, which is a continuation-in-part of U.S. Ser. No. 09/922,333, now U.S. Pat. No. 6,716,979, filed Aug. 4, 2001, which claims priority to U.S. Ser. No. 60/223,086, filed Aug 4, 2000, the disclosures of which are herein incorporated by reference.

FIELD OF THE INVENTION

The invention relates to colored and fluorescent dyes, including reactive dye derivatives, and dye-conjugates; and to their use in staining samples and detecting ligands or other analytes.

BACKGROUND OF THE INVENTION

Fluorescent dyes are known to be particularly suitable for applications in which a highly sensitive detection reagent is desirable. Fluorescent dyes are used to impart both visible color and fluorescence to other materials. As researchers increasingly utilize fluorescent probes as research tools, the ability to select the wavelength of fluorescence becomes more important, particularly as more multiple-color applications are developed.

A variety of fluorescent dyes have been previously and extensively described, including coumarins, fluoresceins, rhodamines, rhodols, oxazines, carbocyanines, and derivatives thereof. The selection of certain substituents has been shown to be useful in adjusting the spectral properties of such dyes but there have remained regions of the visible spectrum where suitable fluorescent dyes either did not exist, or did not possess particularly favorable properties.

The dyes of the invention incorporate additional fused aromatic or heteroaromatic rings, and exhibit a shift of fluorescence emission to longer wavelength that is typically greater than 20 nm, relative to otherwise structurally similar dyes known in the art. This bathochromic spectral shift yields dyes that are particularly useful for excitation in the wavelength ranges between 400 nm and 600 nm and in particular at greater than 630 nm. Of particular importance are the dyes of the invention that exhibit absorbance maxima between 530 nm and 650 nm, as they match the principal emission lines of the mercury arc lamp (546 nm), frequency-doubled Nd-Yag laser (532 nm), Kr-ion laser (568 nm, and 647 nm) and HeNe laser (543 nm, 594 nm, and 633 nm).

Fluorescent dyes of the invention with longer wavelength absorption and emission are particularly useful in conjunction with materials of biological origin such as blood, urine, fecal matter, cells and tissues, because background or inherent fluorescence or absorption is less likely to interfere with dye detection. Furthermore, infrared dyes of the invention have enhanced utility in biological systems that are transparent at infrared wavelengths. The long wavelength dyes of the invention also have advantages in use as laser dyes, or in electronics as optical memory elements using relatively low cost illumination sources such as laser diodes.

DETAILED DESCRIPTION OF THE INVENTION

Introduction

Figure 1:
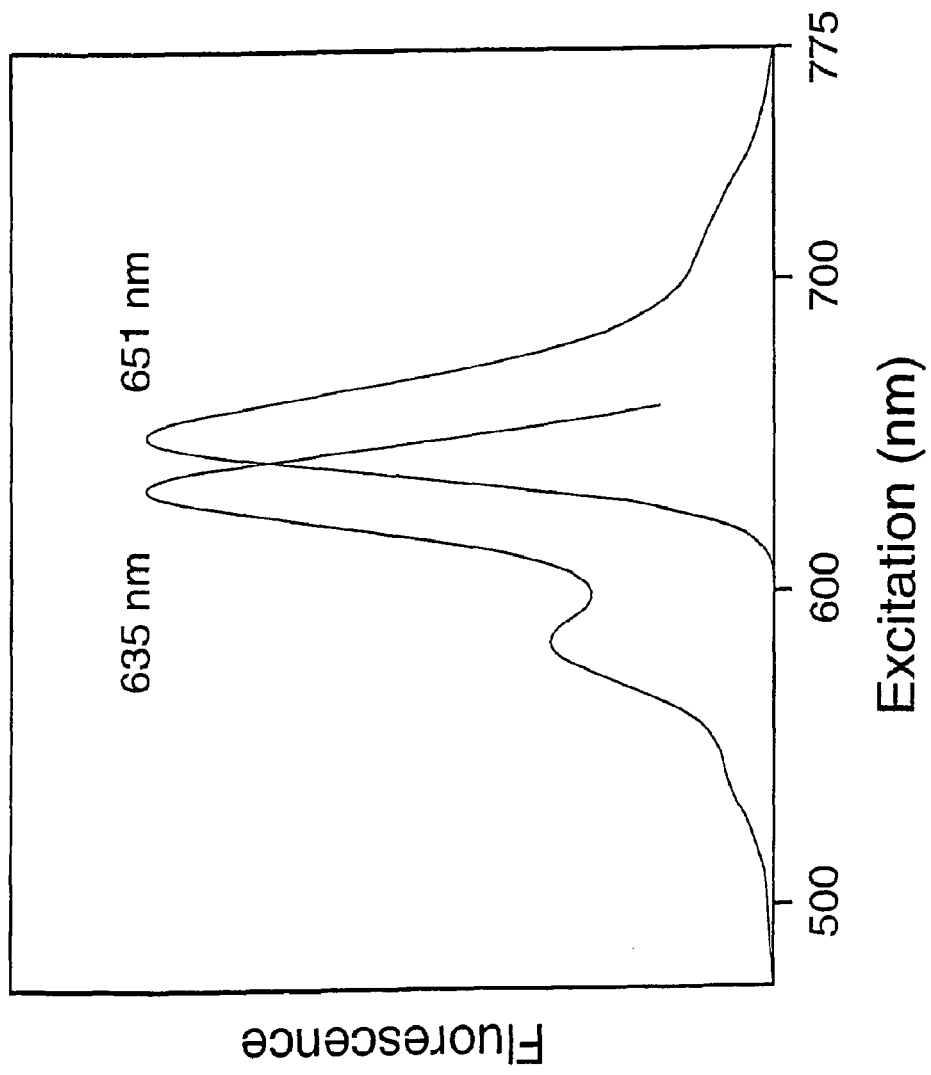
FIG. 1: The excitation and emission spectra of a streptavidin conjugate of Compound 42.

The present invention describes derivatives of 1,2-dihydro-7-hydroxyquinoline useful for the preparation of a variety of fluorescent dyes and dye derivatives. In the derivatives described herein, the 3,4-double bond of the dihydroquinoline is fused to an aromatic or heteroaromatic ring that is in turn optionally fused to one or more additional aromatic or heteroaromatic rings. The invention also includes dyes that are prepared from the novel synthetic precursors, including, but not limited to, coumarin compounds, rhodamine compounds, rhodol compounds, triarylmethane compounds, phenoxazine compounds, and their benzo and annelated derivatives. The dyes of the invention optionally possess a reactive group useful for preparing fluorescent conjugates, which conjugates and methods for their preparation and use are described herein.

DEFINITIONS

Before describing the present invention in detail, it is to be understood that this invention is not limited to specific compositions or process steps, as such may vary. It must be noted that, as used in this specification and the appended claims, the singular form "a", "an" and "the" includes plural referents unless the context clearly dictates otherwise. Thus, for example, reference to "a fluorescent dye" includes a plurality of dyes and reference to "a compound" includes a plurality of compounds and the like.

Unless defined otherwise, all technical and scientific terms used herein have the same meaning as commonly understood by one of ordinary skill in the art to which this invention is related. The following terms are defined for purposes of the invention as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

Although typically not shown for the sake of clarity, any overall positive or negative charges possessed by any of the compounds of the invention are balanced by a necessary counterion or counterions. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylborate, nitrate, hexafluorophosphate, and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty-five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally be quaternized, and the sulfur atoms are optionally trivalent with alkyl or heteroalkyl substituents. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 4 rings), which are fused together or linked covalently. Specific examples of aryl substituents include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Preferred aryl substituents are phenyl, substituted phenyl, naphthyl or substituted naphthyl.

The term "heteroaryl" as used herein refers to an aryl group as defined above in which one or more carbon atoms have been replaced by a non-carbon atom, especially nitrogen, oxygen, or sulfur. For example, but not as a limitation, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, indolizinyl, indazolyl, quinolizinyl, qunolinyl, isoquinolinyl, cinnolinyl, phthalazinyl, quinazolinyl, quinoxalinyl, pteridinyl, quinuclidinyl, carbazolyl, acridinyl, phenazinyl, phenothizinyl, phenoxazinyl, purinyl, benzimidazolyl and benzthiazolyl and their aromatic ring-fused analogs. Many fluorophores are comprised of heteroaryl groups and include, without limitations, xanthenes, oxazines, benzazolium derivatives (including cyanines and carbocyanines), borapolyazaindacenes, benzofurans, indoles and quinazolones.

Where a ring substituent is a heteroaryl substituent, it is defined as a 5- or 6-membered heteroaromatic ring that is optionally fused to an additional six-membered aromatic ring(s), or is fused to one 5- or 6-membered heteroaromatic ring. The heteroaromatic rings contain at least 1 and as many as 3 heteroatoms that are selected from the group consisting of O, N or S in any combination. The heteroaryl substituent is bound by a single bond, and is optionally substituted as defined below.

Specific examples of heteroaryl moieties include, but are not limited to, substituted or unsubstituted derivatives of 2- or 3-furanyl; 2- or 3-thienyl; N-, 2- or 3-pyrrolyl; 2- or 3-benzofuranyl; 2- or 3-benzothienyl; N-, 2- or 3-indolyl; 2-, 3- or 4-pyridyl; 2-, 3- or 4-quinolyl; 1-, 3-, or 4-isoquinolyl; 2-, 4-, or 5-(1,3-oxazolyl); 2-benzoxazolyl; 2-, 4-, or 5-(1,3-thiazolyl); 2-benzothiazolyl; 3-, 4-, or 5-isoxazolyl; N-, 2-, or 4-imidazolyl; N-, or 2-benzimidazolyl; 1- or 2-naphthofuranyl; 1- or 2-naphthothienyl; N-, 2- or 3-benzindolyl; 2-, 3-, or 4-benzoquinolyl; 1-, 2-, 3-, or 4-acridinyl. Preferred heteroaryl substituents include substituted or unsubstituted 4-pyridyl, 2-thienyl, 2-pyrrolyl, 2-indolyl, 2-oxazolyl, 2-benzothiazolyl or 2-benzoxazolyl.

The above heterocyclic groups may further include one or more substituents at one or more carbon and/or non-carbon atoms of the heteroaryl group, e.g., alkyl; aryl; heterocycle; halogen; nitro; cyano; hydroxyl, alkoxyl or aryloxyl; thio or mercapto, alkyl- or arylthio; amino, alkyl-, aryl-, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or arylsulfonyl; hydroximinyl, or aryl- or alkoximinyl. In addition, two or more alkyl substituents may be combined to form fused heterocycle-alkyl ring systems. Substituents including heterocyclic groups (e.g., heteroaryloxy, and heteroaralkylthio) are defined by analogy to the above-described terms.

The term "heterocycloalkyl" as used herein refers to a heterocycle group that is joined to a parent structure by one or more alkyl groups as described above, e.g., 2-piperidylmethyl, and the like. The term "heterocycloalkyl" refers to a heteroaryl group that is joined to a parent structure by one or more alkyl groups as described above, e.g., 2-thienylmethyl, and the like.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

The aryl and heteroaryl substituents described herein are unsubstituted or optionally and independently substituted by H, halogen, cyano, sulfonic acid, carboxylic acid, nitro, alkyl, perfluoroalkyl, alkoxy, alkylthio, amino, monoalkylamino, dialkylamino or alkylamido.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "attachment site" as used herein refers to a site on a moiety or a molecule, e.g. a quencher, a fluorescent dye, an avidin, or an antibody, to which is covalently attached, or capable of being covalently attached, to a linker or another moiety. The term "aqueous solution" as used herein refers to a solution that is predominantly water and retains the solution characteristics of water. Where the aqueous solution contains solvents in addition to water, water is typically the predominant solvent.

The term "BAPTA" as used herein refers to a metal-chelating compound that is 1,2-bis(2-aminophenoxy)ethane-N,N,N'N'-tetraacetic acid or its analogs, derivatives, ring-fused variants and conjugates, and all metallic and nonmetallic salts, partial salts and hydrates thereof, including any corresponding compounds disclosed in U.S. Pat. Nos. 4,603,209; 4,849,362; 5,049,673; 5,453,517; 5,459,276; 5,516,911; 5,501,980; 6,162,931 and 5,773,227 (supra). When used generically, "BAPTA" refers to two benzene rings that are joined by a C$_1$-C$_3$ hydrocarbon bridge terminated by oxygen atoms, including methylenedioxy (—OCH$_2$O—), ethylenedioxy (—OCH$_2$CH$_2$O—) or propylenedioxy (—OCH$_2$CH$_2$CH$_2$O—) bridging groups, where each benzene ring is optionally substituted by one or more substituents that adjust the metal ion-binding affinity, solubility, chemical reactivity, spectral properties or other physical properties of the compound. In a preferred embodiment of the present invention "BAPTA" is covalently attached to a chemical moiety A that, in combination with an appropriate trivalent metal ion and an acid, permits detection or isolation of phosphorylated target molecules as a ternary complex. BAPTA derivatives additionally include compounds in which the benzene rings of the BAPTA structure are substituted by or fused to additional aromatic, or heteroaromatic rings.

The term "Linker" or "L", as used herein, refers to a single covalent bond or a series of stable covalent bonds incorporating 1-30 nonhydrogen atoms selected from the group consisting of C, N, O, S and P that covalently attach the phosphate-binding compounds to another moiety such as a chemically reactive group or a phosphorylated target molecule. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a label or phosphorylated target molecule, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, ortho-hydroxcinnamate esters, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

The term "metal chelator" or "metal-chelating moiety" as used herein refers to a chemical moiety that combines with a metal ion to form a chelate ring structure. For the purposes of the present invention the metal chelator has affinity for a metal ion that has simultaneous affinity for the metal chelator and a phosphate target molecule in a moderately acidic environment. Examples of metal-chelating moieties include, but are not limited to, BAPTA, IDA, DTPA and phenanthroline. The metal chelators are optionally substituted by substituents that adjust the ion-binding affinity, solubility, chemical reactivity, spectral properties or other physical properties of the compound provided that the metal chelator is not sulfonated.

The term "photoactivatable reactive group" as used herein refers to a chemical moiety that becomes chemically active by exposure to an appropriate wavelength, typically a UV wavelength. Once activated the reactive group is capable of forming a covalent bond with a proximal moiety on a biological or non-biological component.

The terms "protein" and "polypeptide" are used herein in a generic sense to include polymers of amino acid residues of any length. The term "peptide" is used herein to refer to polypeptides having less than 100 amino acid residues, typically less than 15 amino acid residues. The terms apply to amino acid polymers in which one or more amino acid residues is an artificial chemical analogue of a corresponding naturally occurring amino acid, as well as to naturally occurring amino acid polymers. The peptide or protein may be further conjugated to or complexed with other moieties such as dyes, haptens, radioactive isotopes, natural and synthetic polymers (including microspheres), glass, metals and metallic particles, proteins and nucleic acids.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as a photoactivatable group, carboxylic acid or succinimidyl ester, on the compounds of the present invention that is capable of chemically reacting with a functional group on a different compound to form a covalent linkage resulting in a phosphate-binding labeled component. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

As used herein the term "sulfonic acid" means either —$SO_3H$, or a salt of sulfonic acid. Also as used herein the term "carboxylic acid" means either —COOH, or a salt of carboxylic acid. Appropriate salts of sulfonic and carboxylic acids include, among others, $K^+$, $Na^+$, $Cs^+$, $Li^+$, $Ca^{2+}$, $Mg^{2+}$, ammonium, alkylammonium or hydroxyalkylammonium salts, or pyridinium salts. Alternatively, the counterion of the sulfonic acid or carboxylic acid may form an inner salt with a positively charged atom on the dye itself, typically a quaternary nitrogen atom.

The Compounds

The synthetic precursors have the formula:

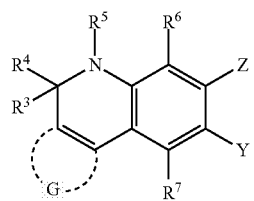

G represents the atoms necessary to form a 5- or 6-membered aromatic or heteroaromatic fused ring, that is optionally substituted one or more times by sulfonic acid, carboxylic acid, or $C_1$-$C_6$ alkyl or alkoxy that is optionally substituted by carboxylic acid, sulfonic acid, or halogen; or by an aryl or heteroaryl ring that is optionally substituted one or more times by $C_1$-$C_6$ alkyl, $C_1$-$C_6$ perfluoroalkyl, cyano, halogen, azido, carboxylic acid, sulfonic acid, or halomethyl. The fused ring G optionally contains one or two additional fused aromatic or heteroaromatic rings that are optionally sulfonated one or more times.

Suitable examples of fused aromatic rings include, but are not limited to, substituted or unsubstituted derivatives of benzenes, naphthalenes, anthracenes, phenanthracenes, or pyrenes. Preferred aromatic rings include substituted or unsubstituted benzene or naphthalenes.

Suitable examples of fused heteroaromatic rings include, but are not limited to, furans, thiophenes, pyrrols, benzofurans, benzothiophenes, indoles, pyridines, quinolines, isoquinolines, oxazoles, benzoxazoles, thiazoles, benzothiazoles, isoxazoles, imidazoles, benzimidazoles, naphthofurans, naphthothiophenes, benzindoles, benzoquinolines, or acridines. Preferred fused heteroaromatic rings include substituted or unsubstituted one or more of $R^1$, $R^2$, and $R^6$ is an aryl or heteroaryl ring that is optionally substituted one or more times by $C_1$-$C_6$ alkyl, $C_1$-$C_6$ perfluoroalkyl, cyano, halogen, azido, carboxylic acid, sulfonic acid, or halomethylpyridines, thiophenes, pyrroles, indoles, oxazoles, benzothiophenes, and benzoxazoles.

$R^6$ is H, cyano, halogen, carboxylic acid, or sulfonic acid, or a $C_1$-$C_6$ alkyl or $C_1$-$C_6$ alkoxy that is optionally substituted by carboxylic acid, sulfonic acid, or halogen. Additionally $R^6$ is an aryl or heteroaryl ring that is optionally substituted one or more times by $C_1$-$C_6$ alkyl, $C_1$-$C_6$ perfluoroalkyl, cyano, halogen, azido, carboxylic acid, sulfonic acid, or halomethyl.

The substituents $R^3$ and $R^4$ are independently H, or a $C_1$-$C_6$ alkyl that is optionally substituted by carboxylic acid, sulfonic acid, amino, hydroxy, or halogen. Alternatively one or both of $R^3$ and $R^4$ is independently an aromatic or heteroaromatic ring that is optionally substituted one or more times by $C_1$-$C_6$ alkyl, $C_1$-$C_6$ alkoxy, $C_1$-$C_6$ perfluoroalkyl, cyano, halogen, carboxylic acid, sulfonic acid, or halomethyl. In another aspect of the invention, $R^3$ and $R^4$, taken in combination, form a 5- or 6-membered ring that optionally contains 1 or 2 heteroatoms. Typically, where $R^3$ and $R^4$ form a ring, it is an alicyclic ring. $R^3$ and $R^4$ are each typically alkyl, and preferably $R^3$ and $R^4$ are methyl.

The $R^5$ substituent is H, methyl, carboxymethyl, or a $C_2$-$C_6$ alkyl that is optionally substituted by carboxylic acid, sulfonic acid, amino, or halogen. Alternatively, $R^5$ is an aryl or heteroaryl ring that is optionally substituted one or more times by $C_1$-$C_6$ alkyl, $C_1$-$C_6$ perfluoroalkyl, cyano, halogen, carboxylic acid, sulfonic acid, or halomethyl. In another aspect of the invention, $R^4$ taken in combination with $R^5$, or $R^5$ taken in combination with $R^6$, forms a 5- or 6-membered alicyclic ring.

The $R^7$ substituent is hydrogen, $C_1$-$C_6$ alkyl, or $C_1$-$C_6$ alkoxy. Typically, $R^7$ is hydrogen.

Y is optionally H, OH, $NH_2$, NO, —(CO)—$R^9$, or —(CO)—O—$R^{10}$, where $R^9$ and $R^{10}$ are H, $C_1$-$C_6$ alkyl, a substituted or unsubstituted aryl or heteroaryl ring system having 1-2 rings.

Z is optionally H, OH, $NHR^{17}$, SH, or $C(CR^{11}R^{12})_2OH$; where $R^{17}$ is a $C_1$-$C_6$ alkyl that is optionally substituted by carboxylic acid, sulfonic acid, amino, or halogen. The $R^{11}$ and $R^{12}$ substituents are independently $C_1$-$C_6$ alkyls that are themselves optionally substituted by carboxylic acid, sulfonic acid, or halogen, or $R^{11}$ and $R^{12}$ taken in combination form a 5- or 6-membered alicyclic ring. Preferably $R^{11}$ and $R^{12}$ are each methyl.

In one embodiment, the synthetic precursor has the formula

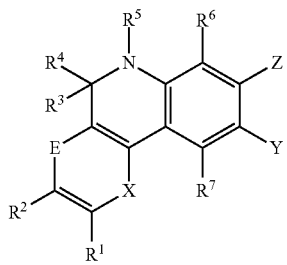

where $R^1$ and $R^2$ are independently selected from H, cyano, halogen, carboxylic acid, or sulfonic acid, or one or more of $R^1$ and $R^2$ may be a $C_1$-$C_6$ alkyl or alkoxy that is optionally substituted by carboxylic acid, sulfonic acid, or halogen. Additionally one or more of $R^1$ and $R^2$ is an aryl or heteroaryl ring that is optionally substituted one or more times by $C_1$-$C_6$ alkyl, $C_1$-$C_6$ perfluoroalkyl, cyano, halogen, azido, carboxylic acid, sulfonic acid, or halomethyl. In another aspect of the invention, $R^1$ in combination with $R^2$ forms a fused aromatic or heteroaromatic ring that is optionally sulfonated one or more times. In another aspect of the invention, $R^2$ taken in combination with $R^3$ forms a 5- or 6-membered alicyclic ring.

One of X and E is selected from O, S, $NR^8$, or $CR^{1'}$=$CR^{2'}$, and the other is absent. The substituent $R^8$ is H, methyl, carboxymethyl, or a $C_2$-$C_6$ alkyl that is optionally substituted by carboxylic acid, sulfonic acid, amino, or halogen. The substituents $R^{1'}$ and $R^{2'}$ are as defined above for $R^1$ and $R^2$. In one embodiment, one of X and E is S or O. In another embodiment, X is O, S, $NR^8$, or $CR^{1'}$=$CR^{2'}$, and E is absent. In yet another embodiment, E is O or S, and X is absent.

Y is optionally H, OH, $NH_2$, NO, —(CO)—$R^9$, or —(CO)—O—$R^{10}$, where $R^9$ and $R^{10}$ are H, $C_1$-$C_6$ alkyl, a substituted or unsubstituted aryl or heteroaryl ring system having 1-2 rings.

Z is optionally H, OH, $NHR^{17}$, SH, or $C(CR^{11}R^{12})_2OH$; where $R^{17}$ is a $C_1$-$C_6$ alkyl that is optionally substituted by carboxylic acid, sulfonic acid, amino, or halogen. The $R^{11}$ and $R^{12}$ substituents are independently $C_1$-$C_6$ alkyls that are themselves optionally substituted by carboxylic acid, sulfonic acid, or halogen, or $R^{11}$ and $R^{12}$ taken in combination form a 5- or 6-membered alicyclic ring.

The precursors of the invention are optionally substituted by a covalently bound reactive group (-L-$R_x$) or conjugated substance (-L-$S_c$) as will be described below. In this embodiment, one or more of $R^1$, $R^2$, $R^3$, $R^4$, $R^5$, $R^6$, $R^7$, $R^8$ is -L-$R_x$ or -L-$S_c$, or where $R^1$ taken in combination with $R^2$ forms a fused aromatic or heteroaromatic ring, the resulting ring is substituted by -L-$R_x$ or -L-$S_c$.

Condensation Reactions of the Novel Precursors

A variety of useful and novel dyes are readily prepared using the precursors of the invention. The dyes of the invention are prepared by condensing a first precursor (a precursor of the invention) with a second precursor, simultaneous with, before, or after reaction with a third precursor. The types of precursors and possible dye products are described in greater detail below. The utilization of the precursors of the invention in these syntheses results in dyes whose absorption is shifted to substantially longer wavelengths, compared to structurally related dyes that do not possess the additional fused ring systems.

Derivatives of 3-aminophenol are valuable synthetic intermediates in the synthesis of a variety of dyes. Numerous classes of commercially important dyes may be prepared with appropriately substituted 3-minophenols using well known synthetic strategies. In particular, 3-aminophenols have been utilized in the preparation of coumarin dyes (U.S. Pat. No. 5,696,157), rhodol dyes (U.S. Pat. No. 5,227,487), rhodamine dyes (U.S. Pat. No. 6,130,101), and oxazine dyes. 3-Aminophenols have also been utilized to prepare annelated rhodol dyes (seminaphthorhodafluor dyes) commercially available under the trademark SNARF (U.S. Pat. No. 4,945,171).

Typically the condensation reaction utilizing the 3-aminophenol derivatives of the invention is acid-catalyzed, and utilizes a first precursor, a second precursor, and optionally utilizes a third precursor. This condensation occurs in the presence or absence of various acid catalysts (such as zinc chloride, p-toluenesulfonic acid, sulfuric acid, or methanesulfonic acid). An aqueous workup, typically followed by column chromatography, yields the desired dye.

The first precursor is a derivative of 3-aminophenol of the invention having the formula

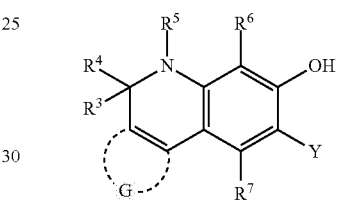

wherein G, $R^3$, $R^4$, $R^5$, and $R^6$ are as defined earlier. $R^7$ is hydrogen or $C_1$-$C_6$ alkyl. Y is optionally H, OH, NO, —(CO)—$R^9$, or —(CO)—O—$R^{10}$, where $R^9$ and $R^{10}$ are H, $C_1$-$C_6$ alkyl, a substituted or unsubstituted aryl or heteroaryl ring system having 1-2 rings.

Typically, the first precursor has the formula

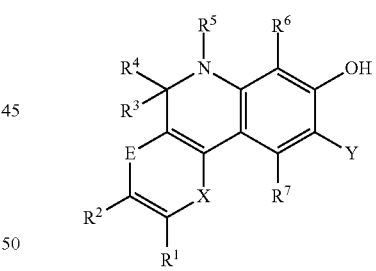

wherein E, X, $R^1$, $R^2$, $R^3$, $R^4$, $R^5$, and $R^6$ are as defined earlier. $R^7$ is hydrogen or $C_1$-$C_6$ alkyl. Y is optionally H, OH, NO, —(CO)—$R^9$, or —(CO)—O—$R^{10}$, where $R^9$ and $R^{10}$ are H, $C_1$-$C_6$ alkyl, a substituted or unsubstituted aryl or heteroaryl ring system having 1-2 rings.

Where Y is NO, the first precursor is a 6-nitroso-3-aminophenol derivative. Where Y is —(CO)—$R^9$, the first precursor is a 6-acyl-3-aminophenol derivative.

The second precursor is permitted to be a 3-aminophenol (to yield a rhodamine), a resorcinol (to yield a rhodol), a 1,6-naphthalenediol (to yield an annelated rhodol), a 6-amino-1-naphthol (to yield an annelated rhodamine), an alpha-methylene acid, an alpha methylene ester, an alpha-methylene nitrile, or a beta-keto ester (all of which yield coumarins). Generic examples of each of these types of precursors are given below, although a variety of substitutions and variations are permissible without effectively diminishing the efficacy of the condensation reaction:

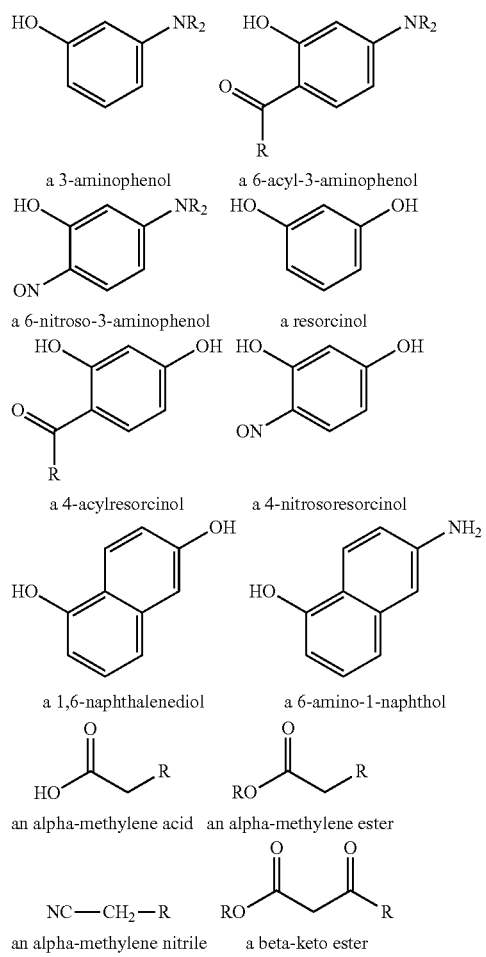

The condensation reaction optionally incorporates a third precursor. The third precursor is typically an aldehyde or an acid, including diacids, acid anhydrides, esters, acid halides and similar acylating agents derived from acids. Examples of aldehydes include formaldehyde, lower aliphatic and alicyclic aldehydes, heterocyclic aldehydes and especially benzaldehydes and less preferably naphthaldehydes. Most commonly the third precursor is an aliphatic or aromatic diacid, or a cyclic anhydride of an aliphatic or aromatic diacid. Particularly preferred third precursors are derivatives of succinic acid, glutaric acid, phthalic acid, or ortho-sulfobenzoic acid.

In those condensation reactions where the third precursor is present, the reaction of the first, second and third precursors is typically a stepwise reaction. The third precursor reacts with either the first or second precursor to form an intermediate condensation product, which then reacts with the remaining precursor.

Where the first and second precursors are the same, the resulting dye is symmetric. Typically, where symmetric dyes are prepared, the condensation includes a third precursor, as described above. Commonly one molecule of a substituted or unsubstituted phthalic acid or anhydride or a substituted or unsubstituted ortho-sulfobenzaldehyde or ortho-sulfobenzoic acid (the third precursor) is condensed with at least two molecules of a 3-aminophenol of the invention (first and second precursor, which are the same) to produce a symmetric rhodamine dye. Less commonly a 3-aminophenol of the invention (first precursor) and a resorcinol or a different 3-aminophenol (second precursor) is condensed with a substituted or unsubstituted phthalic acid or o-sulfobenzoic acid derivative (third precursor) to produce rhodol or asymmetric rhodamine dyes of the invention.

Where the first precursor is a 6-nitroso-3-aminophenol, and the second precursor is a resorcinol or a 3-aminophenol, the resulting dye is an oxazine. Alternatively, the second precursor is nitroso-substituted, such as a 4-nitrosoresorcinol or a 6-nitroso-3-aminophenol. In either case, the resulting product is an oxazine dye.

To prepare coumarin dyes, a first precursor that is a 6-acyl-3-aminophenol is reacted with a second precursor that is an alpha-methylene acid, ester, or nitrile to yield a 3-substituted coumarin, the nature of the 3-substituent of the resulting coumarin dye being dependent upon the 6-acyl moiety on the first precursor. 4-Substituted coumarin dyes are prepared using a first precursor that is a 3-aminophenol of the invention with a second precursor that is a beta-keto ester. In this instance, the nature of the 4-substituent is dependent upon beta-keto ester selected.

Selected condensation reactions of the invention are outlined in Table 1, below.

TABLE 1

| First Precursor | Second Precursor | Third Precursor | Product Dye | Examples |
| --- | --- | --- | --- | --- |
| a 3-aminophenol | a 3-aminophenol | an aldehyde, acid, diacid, or anhydride | a symmetric or asymmetric rhodamine | 18, 29, 30, 32, 33, 36 |
| a 3-aminophenol | a 6-acyl-3-aminophenol | none | | |
| a 6-acyl-3-aminophenol | a 3-aminophenol | none | | |
| a 3-aminophenol | a resorcinol | an aldehyde, acid, diacid, or anhydride | a rhodol | 35 |
| a 6-acyl-3-aminophenol | a resorcinol | none | | |
| a 3-aminophenol | a 4-acylresorcinol | none | | |
| a 3-aminophenol | a 4-nitrosoresorcinol, or a 6-nitroso-3-aminophenol | none | an oxazine | 21 |
| a 6-nitroso-3-aminophenol | a resorcinol, or a 3-aminophenol | none | | |
| a 3-aminophenol | a 1,6-naphthalenediol, or 6-amino-1-naphthol | an aldehyde, acid, diacid, or anhydride | an annelated rhodol or rhodamine | 38 |
| a 6-nitroso-3-aminophenol | a 1,6-naphthalenediol, or a 6-amino-1-naphthol | none | an annelated oxazine | |

TABLE 1-continued

| First Precursor | Second Precursor | Third Precursor | Product Dye | Examples |
| --- | --- | --- | --- | --- |
| a 6-acyl-3-aminophenol | an alpha-methylene acid, ester or nitrile | none | a 3-substituted coumarin | 20 |
| a 3-aminophenol | a beta-keto ester | none | a 4-substituted coumarin | |

In addition to the rhodamine, annelated rhodamine, rhodol, annelated rhodol, oxazine, annelated oxazine and coumarin dyes whose synthesis and properties is described in this invention, first precursors wherein Z is not hydroxy are useful synthetic precursors a variety of analogous classes of dyes. Precursors wherein Z is SH are useful for preparing thiocoumarins, thiorhodamines, thiooxazines and thiorhodols (for example as in EP 0 330 444 to Chen et al., (1989)) and their annelated versions. Precursors wherein Z is $NHR^{17}$ are useful for preparing "azacoumarins" (carbostyryls), "azarhodamines" (acridines), "azarhodols" (acridines), "azaoxazines" (phenazines) and their annelated versions. Precursors wherein Z is $C(CR^{11}R^{12})_2OH$ are useful for preparing carbazine dyes and their analogs. Precursors wherein Z is H are useful for preparing triarylmethane dyes and their analogs (Example 34).

In one aspect of the invention, the resulting dye is sulfonated. Sulfonation can be done subsequent to the condensation reaction (as in Example 23), or one or more precursors may be sulfonated prior to formation of the dye (as for Compound 34 in Example 18).

Sulfonation of dyes is typically carried out by stirring the dye in fuming sulfuric acid (20-30% $SO_3$ content) or concentrated sulfuric acid at an appropriate temperature. Monosulfonation of rhodol dyes is carried out by stirring the appropriate rhodol dye in fuming sulfuric acid at 0° C. for several hours. Bis-sulfonation of rhodols at both the 4'- and 5'- positions, if available, is achieved by stirring the dye in fuming sulfuric acid at room temperature for several hours. Sulfonation of most rhodamine or rosamine dyes at the 4'- and 5'- positions, if available, is carried out with fuming sulfuric acid at 0° C.; the sulfonation is usually complete as soon as a homogeneous solution is achieved during stirring.

Post-condensation modification of xanthene-based dyes is well known. For example, the xanthene portion of the dye can be halogenated by treatment with the appropriate halogenating agent, such as liquid bromine. Xanthenes containing unsaturated fused rings can be hydrogenated to the saturated derivatives. When trimellitic anhydride, nitrophthalic anhydride, or their derivatives are used in the dye synthesis, two isomeric carboxylates or nitro derivatives are typically formed. These isomers are separated or, in most cases, used as the mixture of isomers. The reduced derivatives of xanthylium dyes are typically prepared by chemical reduction of the xanthenone portion with zinc dust, borohydride in organic solvents, or by catalytic hydrogenation. The amino and hydroxyl groups of the dyes of the invention can be acylated or alkylated to yield amides, esters and ethers. Selected amide, ether and ester derivatives of the invention possess potential utility as chromogenic or fluorogenic enzyme substrates.

The selection of an appropriate polyhalogenated phthalic acid derivative or benzaldehyde in the condensation of the xanthylium dye results in a dye having a tetra- or pentachlorinated or tetra- or pentafluorinated phenyl ring at the 9-position. These polyhaloaryl substituted dyes have been shown to react with thiols via a displacement reaction, and thereby provide a facile method of introducing additional reactive groups (Example 19; and as discussed by Gee, et al. TET. LETT. 37, 7905 (1996)).

The dihydroxanthene and xanthylium versions of the dyes of the invention are freely interconvertible by well-known oxidation or reduction reagents, including borohydrides, aluminum hydrides, hydrogen/catalyst, and dithionites. A variety of oxidizing agents mediate the oxidation of dihydroxanthenes, including molecular oxygen in the presence or absence of a catalyst, nitric oxide, peroxynitrite, dichromate, triphenylcarbenium and chloranil. The xanthenes are also oxidized by enzyme action, including horseradish peroxidase in combination with peroxides. Dihydroxanthene dye precursors may also be oxidized inside certain living cells, yielding the corresponding dye compound.

Examples of synthetic strategies for selected dyes of the invention, as well as their characterization, synthetic precursors, conjugates and method of use are provided in the examples below.

Selected Dye Embodiments

In one aspect of the invention, the dyes of the invention that result from the condensation reaction with the precursors described above have the formula

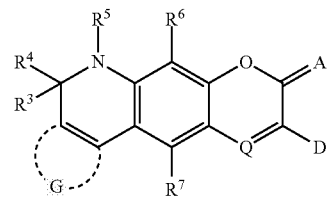

wherein G, $R^3$, $R^4$, $R^6$, and $R^7$ are as described above for the novel precursors of the invention.

The Q moiety is N or $CR^{28}$, wherein $R^{28}$ is H, F, CN, a carboxylic acid, a salt of carboxylic acid, or a carboxylic acid ester of a $C_1$-$C_6$ alcohol. Alternatively $R^{28}$ is a $C_1$-$C_6$ alkyl that is optionally substituted one or more times by carboxylic acid, sulfonic acid, amino, or halogen. In another preferred embodiment, Q is $CR^{28}$ where $R^{28}$ has the formula

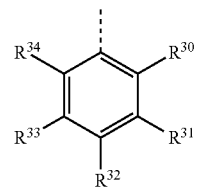

where the substituents $R^{30}$, $R^{31}$, $R^{32}$, $R^{33}$ and $R^{34}$ are independently H, F, Cl, Br, I, sulfonic acid, carboxylic acid, CN, nitro, hydroxy, azido, amino, hydrazino, $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_7$-$C_{18}$ arylcarboxamido. Where any of the $R^{30}$, $R^{31}$, $R^{32}$, $R^{33}$ and $R^{34}$ substituents are alkyl, alkoxy, alkylthio, alkanoylamino, alkylaminocarbonyl, dialkylaminocarbonyl, alkyloxycarbonyl, or arylcarboxamido, the alkyl or aryl portions of the substituents are optionally substituted one or more times by F, Cl, Br, I, hydroxy, carboxylic acid, a carboxylic acid ester of a $C_1$-$C_6$ alcohol, sulfonic acid, amino, alkylamino, dialkylamino or alkoxy (the alkyl portions of each having 1-6 carbons). Alternatively, one pair of adjacent substituents $R^{31}$ and $R^{32}$, $R^{32}$ and $R^{33}$ or $R^{33}$ and $R^{34}$, when taken in combination, form a fused 6-membered aromatic ring that is optionally further substituted by carboxylic acid. Alternatively, one or more of $R^{30}$, $R^{31}$, $R^{32}$, $R^{33}$ and $R^{34}$ is -L-$R_x$ or -L-$S_c$, as described below. In a preferred embodiment, at least one of $R^{30}$, $R^{31}$, $R^{32}$, $R^{33}$ and $R^{34}$ is a -L-$S_c$, wherein L is a single covalent bond and Sc is a metal chelating moiety.

In one aspect of the invention, the resulting dye is a coumarin. In this embodiment, A is O, and D is a monovalent substituent. In another aspect of the invention, A and D, when taken in combination, form an aromatic or heteroaromatic ring system having 1-3 additional rings, where the ring system is optionally substituted.

In one aspect of the invention, the dye of the invention is a coumarin dye having the formula

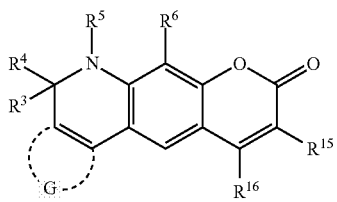

where $GR^3$, $R^4$, $R^5$, and $R^6$ are as defined above.

The substituents $R^{15}$ and $R^{16}$ are independently hydrogen, cyano, nitro, halogen, carboxylic acid, sulfonic acid, or a $C_1$-$C_6$ alkyl that is optionally substituted by carboxylic acid, sulfonic acid, or halogen. Alternatively, one or more of $R^{15}$ and $R^{16}$ is an aromatic or heteroaromatic ring system having 1-2 fused rings that is optionally substituted one or more times by $C_1$-$C_6$ alkyl, $C_1$-$C_6$ perfluoroalkyl, cyano, halogen, carboxylic acid, sulfonic acid, or halomethyl. In another aspect of the invention, one of $R^{15}$ and $R^{16}$ is -L-$R_x$ or -L-$S_c$.

In one aspect of the invention, one of $R^{15}$ and $R^{16}$ is nonhydrogen. In another aspect of the invention, both $R^{15}$ and $R^{16}$ are nonhydrogen. In one aspect of the invention, $R^{16}$ is H. In another aspect of the invention, $R^{16}$ is chloromethyl or bromomethyl. In yet another aspect of the invention, $R^5$ is not hydrogen, and $R^6$ is methyl or $C_1$-$C_6$ alkyl optionally substituted by sulfonic acid or carboxylic acid. Where one of $R^{15}$ or $R^{16}$ is a heteroaromatic ring system, it is typically a benzothiazole.

In another aspect of the invention, the dye of the invention is a derivative of a xanthene or oxazine dye having the formula

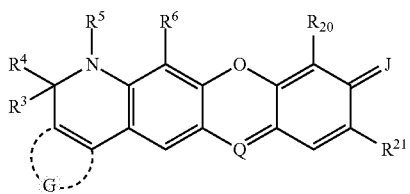

where G, $R^3$, $R^4$, $R^5$, and $R^6$ are as defined above.

The substituents $R^{20}$ and $R^{21}$ are hydrogen, cyano, halogen, carboxylic acid, sulfonic acid, or a $C_1$-$C_6$ alkyl or $C_1$-$C_6$ alkoxy that is itself optionally substituted by carboxylic acid, sulfonic acid, or halogen. Alternatively, one or both of $R^{20}$ and $R^{21}$ is an aromatic or heteroaromatic ring that is optionally substituted one or more times by $C_1$-$C_6$ alkyl, $C_1$-$C_6$ perfluoroalkyl, cyano, halogen, carboxylic acid, sulfonic acid, or halomethyl. Either or both of $R^{20}$ and $R^{21}$ is optionally -L-$R_x$; or -L-$S_c$.

The J moiety is O or $NR^{37}R^{38}$, where $R^{37}$ and $R^{38}$ are independently H or a $C_1$-$C_6$ alkyl that is optionally substituted by carboxylic acid, sulfonic acid, amino, or halogen. Alternatively, one or more of $R^{37}$ and $R^{38}$ is -L-$R_x$ or -L-$S_c$.

Alternatively one of $R^{37}$ and $R^{38}$ is an aryl or heteroaryl ring, or $R^{37}$ when taken in combination with $R^{38}$ forms a saturated 5- or 6-membered heterocycle that is a piperidine, a morpholine, a pyrrolidine or a piperazine, wherein the heterocycle is optionally substituted by methyl, carboxylic acid, or a carboxylic acid ester of a $C_1$-$C_6$ alkyl.

In yet another alternative, $R^{37}$ taken in combination with $R^{20}$, or $R^{38}$ taken in combination with $R^{21}$, or both, form a 5- or 6-membered ring that is saturated or unsaturated, and is optionally substituted by one or more sulfonic acids, or by one or more $C_1$-$C_6$ alkyl groups that are optionally substituted by sulfonic acid.

Q is N or $CR^{28}$, as described above.

In another aspect of the invention, the dye of the invention is a seminaphthorhodafluor derivative having the formula

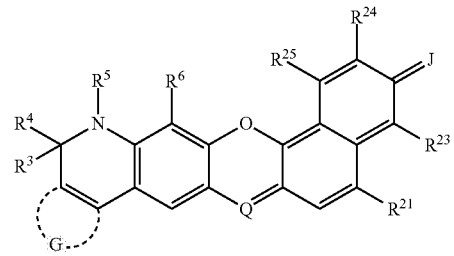

where G, $R^3$, $R^4$, $R^5$, $R^6$, and Q are as defined above.

The substituents $R^{21}$, $R^{23}$, $R^{24}$, and $R^{25}$ are hydrogen, cyano, nitro, halogen, carboxylic acid, or sulfonic acid, or a $C_1$-$C_6$ alkyl that is optionally substituted by carboxylic acid, sulfonic acid, or halogen. Alternatively one or more of $R^{21}$, $R^{23}$, $R^{24}$, and $R^{25}$ is an aromatic or heteroaromatic ring that is optionally substituted one or more times by $C_1$-$C_6$ alkyl, $C_1$-$C_6$ perfluoroalkyl, cyano, halogen, carboxylic acid, sulfonic acid, or halomethyl. Additionally, one or more of $R^{21}$, $R^{23}$, $R^{24}$, and $R^{25}$ is -L-$R_x$ or -L-$S_c$.

The J moiety is O or $NR^{37}R^{38}$, where $R^{37}$ and $R^{38}$ are independently H or a $C_1$-$C_6$ alkyl that is optionally substituted by carboxylic acid, sulfonic acid, amino, or halogen. Alternatively, one or more of $R^{37}$ and $R^{38}$ is -L-$R_x$ or -L-$S_c$.

Derivatives of seminaphthorhodafluor are typically useful as fluorescent pH indicators (see Example 44).

In yet another aspect of the invention, the dye product incorporates two precursor compounds of the invention to yield a rhodamine dye having the formula

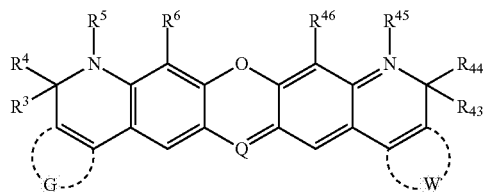

where G, $R^3$, $R^4$, $R^5$, $R^6$, and Q are as defined above.

The substituent $R^{46}$ is H, cyano, halogen, carboxylic acid, sulfonic acid, or $C_1$-$C_6$ alkyl or alkoxy that is optionally substituted by carboxylic acid, sulfonic acid, or halogen. Alternatively $R^{46}$ is an aryl or heteroaryl ring that is optionally substituted one or more times by $C_1$-$C_6$ alkyl, $C_1$-$C_6$ perfluoroalkyl, cyano, halogen, azido, carboxylic acid, sulfonic acid, or halomethyl. $R^{46}$ may also be -L-$R_x$ or -L-$S_c$.

The substituents $R^{43}$ and $R^{44}$ are independently H, or a $C_1$-$C_6$ alkyl that is optionally substituted by carboxylic acid, sulfonic acid, amino, hydroxy, or halogen. Alternatively one or both of $R^{43}$ and $R^{44}$ is independently an aromatic or heteroaromatic ring that is optionally substituted one or more times by $C_1$-$C_6$ alkyl, $C_1$-$C_6$ alkoxy, $C_1$-$C_6$ perfluoroalkyl, cyano, halogen, carboxylic acid, sulfonic acid, or halomethyl. $R^{43}$ and $R^{44}$ are each typically alkyl, and preferably $R^{43}$ and $R^{44}$ are methyl. In another aspect of the invention, $R^{43}$ taken in combination with $R^{44}$, forms a 5- or 6-membered alicyclic ring. Alternatively, $R^{43}$ and $R^{44}$ are -L-$R_x$ or -L-$S_c$.

The $R^{45}$ substituent is H, methyl, carboxymethyl, or a $C_2$-$C_6$ alkyl that is optionally substituted by carboxylic acid, sulfonic acid, amino, or halogen. Alternatively, $R^{45}$ is an aryl or heteroaryl ring that is optionally substituted one or more times by $C_1$-$C_6$ alkyl, $C_1$-$C_6$ perfluoroalkyl, cyano, halogen, carboxylic acid, sulfonic acid, or halomethyl. In another aspect of the invention, $R^{44}$ taken in combination with $R^{45}$, or $R^{45}$ taken in combination with $R^{46}$, forms a 5- or 6-membered alicyclic ring. Alternatively, $R^{45}$ is -L-$R_x$ or -L-$S_c$.

The fused ring W is a 5- or 6-membered aromatic or heteroaromatic fused ring that has the same parameters defined for G above, and is optionally the same as or different from G.

In one embodiment, the fused ring W has the formula

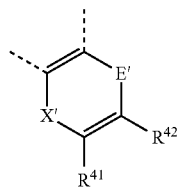

where X' and E' are defined as for X and E above, and $R^{41}$ is defined as $R^1$ above, and $R^{42}$ is defined as $R^2$ above.

Typically, in this embodiment, the dye is fully symmetrical. That is, G and W are the same. In particular, X=X', E=E', $R^1$=$R^{41}$, and $R^2$=$R^{42}$. In a fully symmetrical dye, $R^3$ and $R^{43}$ are the same, $R^4$ and $R^{44}$ are the same, $R^5$ and $R^{45}$ are the same, and $R^6$ and $R^{46}$ are the same. In another aspect of the invention, $R^3$, $R^4$, $R^{43}$, and $R^{44}$ are each methyl. In one preferred embodiment, each X is S, and each $R^1$ is sulfonic acid.

In one embodiment, the dyes of the invention are derivatives of 3- and/or 6-amino xanthenes that are substituted at one or more amino nitrogen atoms by an aromatic or heteroaromatic ring system (i.e., one or more of $R^5$, $R^{37}$, and $R^{38}$ is an aromatic or heteroaromatic ring). N-aryl rhodamines have been shown to be efficient and minimally fluorescent energy acceptors (U.S. Pat. No. 6,399,392), and such compounds are useful in any application where a quenching energy acceptor is useful, particularly in applications utilizing fluorescence resonance energy transfer (FRET). In a preferred embodiment, one or more of $R^5$, $R^{37}$ and $R^{38}$ is phenyl.

In another embodiment of the invention, the dyes have the formula:

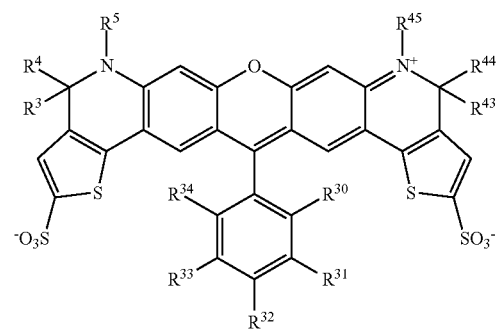

wherein $R^3$, $R^4$, $R^5$, $R^{43}$, $R^{44}$, and $R^{45}$ are independently methyl or ethyl;

$R^{30}$ is sulfonic acid or carboxylic acid;

$R^{31}$ and $R^{34}$ are independently H, F, or Cl one of $R^{32}$ and $R^{33}$ is H, F, or Cl, and the other of $R^{32}$ and $R^{33}$ is -L-$R_x$ or -L-$S_c$, wherein L is a covalent linkage of the formula —S(CH$_2$)$_a$COO(CH$_2$)$_b$— or the formula —S(CH$_2$)$_a$CONH(CH$_2$)$_b$— wherein a is an integer between 0 and 10, and b is an integer between 0 and 10 provided that a and b are not both 0; and $R_x$ and $S_c$ are as defined above. Preferably, $R_x$, where present, is a carboxylic acid, an activated ester of a carboxylic acid, a haloacetamide, a hydrazine, an isothiocyanate, a maleimide group, or a reactive platinum complex; and $S_c$, where present, is an amino acid, a peptide, a protein, an metal chelating moiety, a nucleoside, a nucleotide, an oligonucleotide, or a nucleic acid.

Reduced Dyes

Selected dye embodiments are interconvertible with the reduced, or dihydroxanthene, form of the dye. These dihydroxanthene derivatives having the general structures:

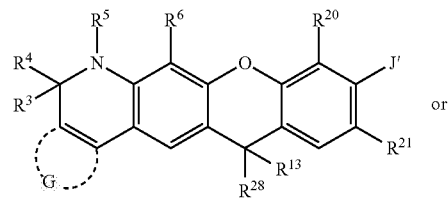

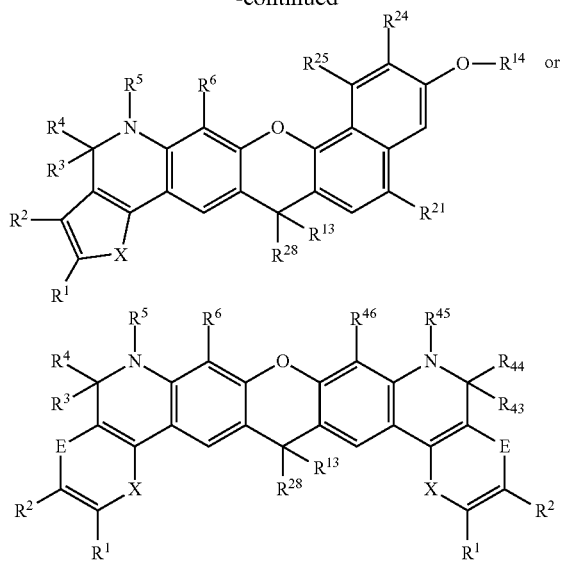

where J' is the same as J, defined above, $R^{28}$ is defined as above, $R^{13}$ is H, hydroxy, CN or a $C_1$-$C_6$ alkoxy, and $R^{14}$ is H, $C_1$-$C_{18}$ alkyl, or -L-$R_x$, or -L-$S_c$. The remaining dye substituents are as defined above.

In another embodiment of the reduced dyes of the invention, wherein $R^{30}$ is a carboxylic acid, or $R^{28}$ is a propionic or butyric acid, may exist in equilibrium with an isomer that incorporates a spirolactone ring. Similarly, reduced dyes wherein $R^{30}$ is a sulfonic acid, or $R^{28}$ is a sulfonic acid-substituted ethyl or propyl may exist in equilibrium with an isomer that incorporates a spirosultone ring. Isomers that incorporate a spirolactone or spirosultone ring are typically non-fluorescent until the ring is opened.

For these embodiments, $R^{13}$ taken in combination with $R^{28}$ forms a 5-membered spirolactone ring or a 5-membered spirosultone ring. Alternatively, $R^{13}$ in combination with $R^{30}$ forms a 5- or 6-membered spirolactone ring or a 5- or 6-membered spirosultone ring.

The dihydroxanthene and xanthylium versions of the dyes of the invention are freely interconvertible by well-known oxidation or reduction reagents, as discussed below.

Conjugates of Reactive Dyes

In another embodiment of the invention, the cyanine dyes of the invention are chemically reactive, and are substituted by at least one group -L-$R_x$, where $R_x$ is the reactive group that is attached to the dye by a covalent linkage L. $R_x$ is a reactive group that functions as the site of attachment for another moiety wherein the reactive group chemically reacts with an appropriate reactive or functional group on another substance or moiety. These reactive groups or reactive precursor are synthesized during the formation of the present compounds providing present compounds that can be covalently attached to another substance, conjugated substance, facilitated by the reactive group. In this way, compounds incorporating a reactive group ($R_x$) can be covalently attached to a wide variety of biomolecules or non-biomolecules that contain or are modified to contain functional groups with suitable reactivity, resulting in chemical attachment of the conjugated substance ($S_c$), represented by -L-$S_c$. In this way, the present dye compounds can function as reporter molecules for the conjugated substance. The reactive group and functional group are typically an electrophile and a nucleophile that can generate a covalent linkage. Alternatively, the reactive group is a photo-activatable group (a benzophenone, an aryl azide or a diazirine), and becomes chemically reactive only after illumination with light of an appropriate wavelength. Typically, the conjugation reaction between the reactive group and the substance to be conjugated results in one or more atoms of the reactive group $R_x$ to be incorporated into a new linkage attaching the compound of the invention to the conjugated substance Sc. Selected examples of functional groups and linkages are shown in Table 2, where the reaction of an electrophilic group and a nucleophilic group yields a covalent linkage.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —CO, where is a good leaving group (e.g. succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates The covalent linkage L binds the reactive group $R_x$ or conjugated substance $S_c$ to the compound, either directly (L is a single bond) or with a combination of stable chemical bonds, optionally including single, double, triple or aromatic carbon-carbon bonds, as well as carbon-nitrogen bonds, nitrogen-nitrogen bonds, carbon-oxygen bonds, carbon-sulfur bonds, phosphorus-oxygen bonds, and phosphorus-nitrogen bonds. L typically includes ether, thioether, carboxamide, sulfonamide, urea, urethane or hydrazine moieties. In one embodiment, the covalent linkage incorporates a platinum atom, such as described in U.S. Pat. No. 5,714,327 (incorporated by reference). Preferred L moieties have 1-20 nonhydrogen atoms selected from the group consisting of C, N, O, P, and S; and are composed of any combination of ether, thioether, amine, ester, carboxamide, sulfonamide, hydrazide bonds and aromatic or heteroaromatic bonds. Preferably L is a combination of single carbon-carbon bonds and carboxamide or thioether bonds. The longest linear segment of the linkage L preferably contains 4-10 nonhydrogen atoms, including one or two heteroatoms. Examples of L include substituted or unsubstituted polymethylene, arylene, alkylarylene, arylenealkyl, or arylthio. In one embodiment, L contains 1-6 carbon atoms; in another, L is a thioether linkage. In yet another embodiment, L is or incorporates the formula $—(CH_2)_a(CONH(CH_2)_b)_z—$, where a has any value from 0-5, b has any value from 1-5 and z is 0 or 1.

The $-L-R_x$ and $-L-S_c$ moieties are bound directly to the fluorophore at any of $R^1$, $R^{1'}$, $R^2$, $R^{2'}$, $R^3$, $R^4$, $R^5$, $R^6$, $R^7$, $R^8$, $R^{15}$, $R^{16}$, $R^{20}$, $R^{21}$, $R^{23}$, $R^{24}$, $R^{25}$, $R^{28}$, $R^{30}$, $R^{31}$, $R^{32}$, $R^{33}$, $R^{34}$, $R^{37}$, $R^{38}$, $R^{41}$, $R^{42}$, $R^{43}$, $R^{44}$, $R^{45}$, or $R^{46}$. In one embodiment, exactly one of $R^{28}$, $R^{30}$, $R^{31}$, $R^{32}$, $R^{33}$ and $R^{34}$ is a $-L-R_x$ or $-L-S_c$ moiety. In another embodiment, one of $R^{37}$ and $R^{38}$ is $-L-R_x$ or $-L-S_c$. In yet another embodiment, $R^{28}$ is $-L-R_x$ or $-L-S_c$. In yet another embodiment, exactly one of $R^{15}$ and $R^{16}$ is a $-L-R_x$ or $-L-S_c$ moiety. In another embodiment, one of $R^1$ and $R^2$ is an $-L-R_x$ and $-L-S_c$. In yet another embodiment, one of $R^3$ and $R^4$ is an $-L-R_x$ or $-L-S_c$.

Choice of the reactive group used to attach the fluorophore to the substance to be conjugated typically depends on the functional group on the substance to be conjugated and the type or length of covalent linkage desired. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one fluorophore, which may be the same or different, or to a substance that is additionally modified by a hapten, such as biotin. Although some selectivity can be obtained by careful control of the reaction conditions, selectivity of labeling is best obtained by selection of an appropriate reactive dye.

Typically, $R_x$ will react with an amine, a thiol, an alcohol, an aldehyde or a ketone. In one embodiment, $R_x$ is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is meant chemically reactive platinum complexes such as described in U.S. Pat. No. 5,714,327.

Where the reactive group is a photoactivatable group, such as an azide, diazirinyl or azidoaryl derivative, the dye becomes chemically reactive only after illumination with light of an appropriate wavelength.

Where $R_x$ is a succinimidyl ester of a carboxylic acid, the reactive dye is particularly useful for preparing dye-conjugates of proteins or oligonucleotides. Where $R_x$ is a maleimide or haloacetamide the reactive dye is particularly useful for conjugation to thiol-containing substances. Where $R_x$ is a hydrazide, the reactive dye is particularly useful for conjugation to periodate-oxidized carbohydrates and glycoproteins, and in addition is an aldehyde-fixable polar tracer for cell microinjection.

Preferably, $R_x$ is a phosphoramidite, a succinimidyl ester of a carboxylic acid, a haloacetamide, a hydrazine, an isothiocyanate, a maleimide group, a perfluorobenzamido, or an azidoperfluorobenzamido group. More preferably, $R_x$ is a phosphoramidite, a reactive platinum complex, or a succinimidyl ester of a carboxylic acid. Where $R_x$ is a reactive platinum complex, it is typically a haloplatinate.

The reactive dyes of the invention are useful for the preparation of any conjugated substance that possess a suitable functional group for covalent attachment of the fluorophore. However, it is appreciated that certain conjugated substances may be covalently bonded to the present dyes wherein a reactive group was not employed to bond together the present compound and the biological or non-biological substance. This is particularly the case, wherein a linker of a single covalent bond attaches the present compound to another chemical moiety, such as a metal chelating moiety.

Examples of particularly useful dye-conjugates include, among others, conjugates of antigens, steroids, vitamins, drugs, haptens, metabolites, toxins, environmental pollutants, amino acids, peptides, proteins, nucleic acids, nucleic acid polymers, carbohydrates, lipids, metal chelating moieties, and non-biological polymers. Alternatively, these are conjugates of cells, cellular systems, cellular fragments, or subcellular particles. Examples include, among others, virus particles, bacterial particles, virus components, biological cells (such as animal cells, plant cells, bacteria, yeast, or protists), or cellular components. Reactive dyes typically label reactive sites at the cell surface, in cell membranes, organelles, or cytoplasm. Preferably the conjugated substance is an amino acid, peptide, protein, tyramine (see Example 42), polysaccharide, metal chelating moiety, nucleoside, nucleotide, oligonucleotide, nucleic acid, hapten, psoralen, drug, hormone, lipid, lipid assembly, polymer, polymeric microparticle, biological cell or virus. In one embodiment, conjugates of biological polymers such as peptides, proteins, oligonucleotides, nucleic acid polymers are also labeled with a second fluorescent or non-fluorescent dye, including an additional dye of the present invention, to form an energy-transfer pair.

In one embodiment, the conjugated substance ($S_c$) is an amino acid (including those that are protected or are substituted by phosphates, carbohydrates, or $C_1$ to $C_{22}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the conjugated protein is an antibody, an antibody fragment, avidin, streptavidin, a toxin, a lectin, a hormone, or a growth factor. Typically where the conjugated substance is a toxin, it is a neuropeptide or a phallotoxin, such as phalloidin.

In another embodiment, the conjugated substance ($S_c$) is a nucleic acid base, nucleoside, nucleotide or a nucleic acid polymer, including those that were modified to possess an additional linker or spacer for attachment of the dyes of the invention, such as an alkynyl linkage (U.S. Pat. No. 5,047,519), an aminoallyl linkage (U.S. Pat. No. 4,711,955) or other linkage. In another embodiment, the conjugated substance is a nucleoside or nucleotide analog that links a purine or pyrimidine base to a phosphate or polyphosphate moiety through a noncyclic spacer (acyclonucleosides and acyclonucleotides). Preferably, the conjugated nucleotide is a nucleoside triphosphate or a deoxynucleoside triphosphate or a dideoxynucleoside triphosphate.

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates (AntiVirals, Inc., Corvallis Oreg.), or peptide nucleic acids such as N-(2-aminoethyl)glycine units. When the nucleic acid is a synthetic oligonucleotide, it typically contains fewer than 50 nucleotides, more typically fewer than 25 nucleotides.

Large fluorescent nucleic acid polymers are typically prepared from labeled nucleotides or oligonucleotides using oligonucleotide-primed DNA polymerization, such as by using the polymerase chain reaction or through primer extension, or by terminal-transferase catalyzed addition of a labeled nucleotide to a 3'-end of a nucleic acid polymer. Typically, the dye is attached via one or more purine or pyrimidine bases through an amide, ester, ether or thioether bond; or is attached to the phosphate or carbohydrate by a bond that is an ester, thioester, amide, ether or thioether. Alternatively, dye conjugate of the invention is simultaneously labeled with a hapten such as biotin or digoxigenin, or to an enzyme such as alkaline phosphatase, or to a protein such as an antibody. Nucleotide conjugates of the invention are readily incorporated by DNA polymerase and can be used for in situ hybridization (Example 62) and nucleic acid sequencing (e.g., U.S. Pat. Nos. 5,332,666; 5,171,534; and 4,997,928; and WO Appl. 94/05688). In another aspect of the invention, the oligonucleotide incorporates an aliphatic amine, which is then conjugated to an amine-reactive dye of the invention. In yet another aspect of the invention, the purine bases of the oligonucleotide react with a reactive platinum complex bound to a dye of the invention, yielding a dye-conjugate (Example 65).

In one embodiment, the conjugated oligonucleotides of the invention are aptamers for a particular target molecule, such as a metabolite, dye, hapten, or protein. That is, the oligonucleotides have been selected to bind preferentially to the target molecule. Methods of preparing and screening aptamers for a given target molecule have been previously described and are known in the art (for example U.S. Pat. No. 5,567,588).

In another embodiment, the conjugated substance ($S_c$) is a carbohydrate that is typically a polysaccharide, such as a dextran, FICOLL, heparin, glycogen, amylopectin, mannan, inulin, starch, agarose and cellulose. Alternatively, the carbohydrate is a polysaccharide that is a lipopolysaccharide. Preferred polysaccharide conjugates are dextran, FICOLL, or lipopolysaccharide conjugates.

In another embodiment, the conjugated substance ($S_c$), is a lipid (typically having 6-60 carbons), including glycolipids, phospholipids, sphingolipids, and steroids. Alternatively, the conjugated substance is a lipid assembly, such as a liposome. The lipophilic moiety may be used to retain the conjugated substances in cells, as described in U.S. Pat. No. 5,208,148. Certain polar dyes of the invention may also be trapped within lipid assemblies.

Conjugates having a metal chelating moiety serve as indicators for calcium, sodium, magnesium, zinc, potassium, gallium, iron, lead or other important metal ions. Preferred metal chelating moieties are crown ethers, including diaryldiaza crown ethers (U.S. Pat. No. 5,405,975); derivatives of 1,2-bis-(2-aminophenoxyethane)-N,N,N',N'-tetraacetic acid (BAPTA chelators; U.S. Pat. Nos. 5,453,517, 5,516,911, and 5,049,673); derivatives of 2-carboxymethoxy-aniline-N,N-diacetic acid (APTRA chelators; AM. J. PHYSIOL. 256, C540 (1989)); or pyridine- and phenanthroline-based metal ion chelators (U.S. Pat. No. 5,648,270). Preferably the metal chelating moiety is a diaryldiaza crown ether, a BAPTA chelator, or an APTRA chelator. These metal chelating moieties are typically bonded to the present compounds by a single bond wherein a reactive group and conjugation reaction was not employed to form the dye-conjugate. Instead these compounds were synthesized utilizing a different strategy, See Example 39 (Compound 59), Example 69 (Compound 65) and Example 70 (Compound 66).

In one aspect of the invention, these metal chelating moieties that are bonded to the present compounds, are substituted by a reactive group. Of particular interest are photoactivatable reactive groups (a benzophenone, an aryl azide or a diazirine) such that a covalent bond can be formed, after activation with an appropriate light source such as a UV light, with a metal ion or metal ion containing compound that is complexed with the metal chelating moiety-dye compound. In this instance, a very specific covalent bond can be formed without the need to purify the sample and allows for indirect labeling of the present dye compounds to a metal ion containing complex. Metal ion containing compounds include, but are not limited to, zinc-binding proteins, calcium binding proteins and other proteins that bind biological and non-biological metal ions.

Alternatively, where the dye is a derivative of a rhodol or a seminaphthorhodafluor (SNARF), the dye itself acts as an indicator of $H^+$ at pH values within about 1.5 pH units of the individual dye's pKa (see Example 44).

Where the conjugated substance of the $-L-S_c$ moiety is a metal chelating moiety, $-L-S_c$ is typically $R^{28}$, or one of $R^{30}$-$R^{34}$. Alternatively, the metal chelating moiety is bound at one of $R^{37}$ or $R^{38}$. The ion indicators are optionally conjugated to plastic or biological polymers such as dextrans or microspheres to improve their utility as sensors.

Other conjugates of non-biological materials include dye-conjugates of organic or inorganic polymers, polymeric films, polymeric wafers, polymeric membranes, polymeric particles, or polymeric microparticles, including magnetic and non-magnetic microspheres, conducting and non-conducting metals and non-metals, and glass and plastic surfaces and particles. Conjugates are optionally prepared by copolymerization of a dye that contains an appropriate functionality while preparing the polymer, or by chemical modification of a polymer that contains functional groups with suitable chemical reactivity. Other types of reactions that are useful for preparing dye-conjugates of polymers include catalyzed polymerizations or copolymerizations of alkenes and reactions of dienes with dienophiles, transesterifications or transaminations. In another embodiment, the conjugated substance is a glass or silica, which may be formed into an optical fiber or other structure.

The preparation of dye conjugates using reactive dyes is well documented, e.g. by R. Haugland, MOLECULAR PROBES HANDBOOK OF FLUORESCENT PROBES AND RESEARCH CHEMICALS, Chapters 1-3 (1996); and Brinkley, BIOCONJUGATE CHEM., 3, 2 (1992). Conjugates typically result from mixing appropriate reactive dyes and the substance to be conjugated in a suitable solvent in which both are soluble. The dyes of the invention are readily soluble in aqueous solutions, facilitating conjugation reactions with most biological materials.

For those reactive dyes that are photoactivated, conjugation requires illumination of the reaction mixture to activate the reactive dye.

Labeled members of a specific binding pair are typically used as fluorescent probes for the complementary member of that specific binding pair, each specific binding pair member having an area on the surface or in a cavity that specifically binds to and is complementary with a particular spatial and polar organization of the other. Preferred specific binding pair members are proteins that bind non-covalently to low molecular weight ligands, such as biotin, drug-haptens and fluorescent dyes (such as an anti-fluorescein antibody). Such probes optionally contain a covalently bound moiety that is removed by an enzyme or light, or the dye is a dihydroxanthene derivative where $R^{13}$ is H and the compound fluoresces following oxidation. Representative specific binding pairs are shown in Table 3.

TABLE 3

Representative Specific Binding Pairs

| antigen | antibody |
|---|---|
| biotin | avidin (or streptavidin or anti-biotin) |
| IgG* | protein A or protein G |
| drug | drug receptor |
| toxin | toxin receptor |
| carbohydrate | lectin or carbohydrate receptor |
| peptide | peptide receptor |
| protein | protein receptor |
| enzyme substrate | enzyme |
| DNA (RNA) | aDNA (aRNA)† |
| hormone | hormone receptor |
| ion | chelator |
| psoralen | nucleic acid |
| target molecule | RNA or DNA aptamer |

*IgG is an immunoglobulin
†aDNA and aRNA are the antisense (complementary) strands used for hybridization In one aspect of the invention, the conjugated substance is further labeled with additional dye moieties, such that fluorescence energy is either accepted from, or transferred to, the dye of the invention. As stated above, N-aryl derivatives of the dyes of the invention have particular utility as quenchers in FRET applications. However, fluorescent dyes of the invention also possess utility as energy donors in FRET applications.

Applications and Methods of Use

In one aspect of the invention, the dye compounds of the invention possess utility as laser dyes according to methods known in the art. As discussed above, the long wavelength properties of the subject dyes allow the use of inexpensive laser diodes as excitation sources for dye lasers utilizing the subject dyes.

In another aspect of the invention, the dye compounds of the invention are used to directly stain or label a sample so that the sample can be identified or quantitated. For instance, such dyes may be added as part of an assay for a biological target analyte, as a detectable tracer element in a biological or non-biological fluid, or for such purposes as photodynamic therapy of tumors, in which a dyed sample is irradiated to selectively destroy tumor cells and tissues, or to photoablate arterial plaque or cells, usually through the photosensitized production of singlet oxygen.

In one aspect of the invention, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

In yet another embodiment, the sample is present on or in solid or semi-solid matrix. In one aspect of the invention, the matrix is a membrane. In another aspect, the matrix is an electrophoretic gel, such as is used for separating and characterizing nucleic acids or proteins. In another aspect, the matrix is a silicon chip or glass slide, and the analyte of interest has been immobilized on the chip or slide in an array. In yet another aspect, the matrix is a microwell plate or microfluidic chip, and the sample is analyzed by automated methods, typically by various methods of high-throughput screening, such as drug screening.

The dye compounds of the invention are generally utilized by combining a dye compound of the invention as described above with the sample of interest under conditions selected to yield a detectable optical response. The term "dye compound" is used herein to refer to all aspects of the claimed dyes, including both reactive and non-reactive dyes and conjugates of dyes. The dye compound typically forms a covalent or non-covalent association or complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard or expected response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic. Some dyes of the invention, such as N-aryl rhodamines and triphenyl methane derivatives, may exhibit little fluorescence emission, but are still useful as chromophoric dyes. Such chromophores are useful as energy acceptors in FRET applications, or to simply impart the desired color to a sample or portion of a sample.

For biological applications, the dye compounds of the invention are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar or more. The optimal concentration is determined by systematic variation until satisfactory results with minimal background fluorescence is accomplished.

The dye compounds are most advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acid, nucleic acid or carbohydrate polymers, or lipid membrane complexes). These dyes are generally non-toxic to living cells and other biological components, within the concentrations of use.

The dye compound is combined with the sample in any way that facilitates contact between the dye compound and the sample components of interest. Typically, the dye compound or a solution containing the dye compound is simply added to the sample. Certain dyes of the invention, particularly those that are substituted by one or more sulfonic acid moieties, tend to be impermeant to membranes of biological cells, and once inside viable cells are typically well retained. Treatments that permeabilize the plasma membrane, such as electroporation, shock treatments or high extracellular ATP can be used to introduce dye compounds into cells. Alternatively, the dye compounds can be physically inserted into cells, e.g. by pressure microinjection, scrape loading, patch clamp methods, or phagocytosis.

Dyes that incorporate an amine or a hydrazine residue can be microinjected into cells, where they can be fixed in place by aldehyde fixatives such as formaldehyde or glutaraldehyde. This fixability makes such dyes useful for intracellular applications such as neuronal tracing.

Dye compounds that possess a lipophilic substituent, such as phospholipids, will non-covalently incorporate into lipid assemblies, e.g. for use as probes for membrane structure; or for incorporation in liposomes, lipoproteins, films, plastics, lipophilic microspheres or similar materials; or for tracing. Lipophilic dyes are useful as fluorescent probes of membrane structure.

Chemically reactive dye compounds will covalently attach to a corresponding functional group on a wide variety of materials, forming dye conjugates as described above. Using dye compounds to label reactive sites on the surface of cells, in cell membranes or in intracellular compartments such as organelles, or in the cell's cytoplasm, permits the determination of their presence or quantity, accessibility, or their spatial and temporal distribution in the sample. Photoreactive dyes can be used similarly to photolabel components of the outer membrane of biological cells or as photo-fixable polar tracers for cells.

Optionally, the sample is washed after staining to remove residual, excess or unbound dye compound. The sample is optionally combined with one or more other solutions in the course of staining, including wash solutions, permeabilization and/or fixation solutions, and solutions containing additional detection reagents. An additional detection reagent typically produces a detectable response due to the presence of a specific cell component, intracellular substance, or cellular condition, according to methods generally known in the art. Where the additional detection reagent has, or yields a product with, spectral properties that differ from those of the subject dye compounds, multi-color applications are possible. This is particularly useful where the additional detection reagent is a dye or dye-conjugate of the present invention having spectral properties that are detectably distinct from those of the staining dye.

The compounds of the invention that are dye conjugates are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. Nos. 5,332,666; 5,171,534; 4,997,928; and WO Appl. 94/05688). Dye-conjugates of multiple independent dyes of the invention possess utility for multi-color applications.

At any time after or during staining, the sample is illuminated with a wavelength of light selected to give a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

Kits

One aspect of the instant invention is the formulation of kits that facilitate the practice of various assays using the dyes of the invention, as described above. The kits of the invention typically comprise a colored or fluorescent dye of the invention, either present as a chemically reactive label useful for preparing dye-conjugates, or present as a dye-conjugate where the conjugated substance is a specific binding pair member, or a nucleoside, nucleotide, oligonucleotide, nucleic acid polymer, peptide, or protein. The kit optionally further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

The examples below are given so as to illustrate the practice of this invention. They are not intended to limit or define the entire scope of this invention.

A detailed description of the invention having been provided above, the following examples are given for the purpose of illustrating the invention and shall not be construed as being a limitation on the scope of the invention or claims.

EXAMPLES

Example 1

Preparation of Compound 1

The following compound is prepared:

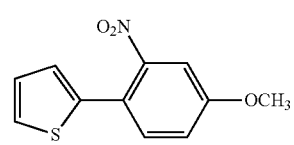

Compound 1

To a flask (250 mL) is added 4-bromo-3-nitroanisole (57.7 mmol), thiophene-2-boronic acid (69.2 mmol), Pd(OAc)$_2$ (4.5 mmol), K$_2$CO$_3$ (14.3 mmol) and Bu$_4$NBr (115 mmol). The flask is flushed with N$_2$ gas and equipped with a rubber septum. To the reaction mixture is added deoxygenated water (120 mL) with a syringe, and the suspension is stirred and degassed to remove residual oxygen. The suspension is stirred and heated for 1 h at 80° C. under $N_2$ gas, then cooled to room temperature and diluted with water. The resulting precipitate is filtered and washed with ethyl acetate. The filtrate is extracted with ethyl acetate, and the combined organic layers are dried over anhydrous $Na_2SO_4$ and volatiles are removed under vacuum to give a brown solid. The crude solid is purified on a silica gel column eluting with hexanes and 5:1 hexanes/ethyl acetate to give Compound 1 (15.2 g).

Compounds 2, 3, and 4 are prepared analogously, using benzothiophene-2-boronic acid and 4-bromo-3-nitroanisole, thiophene-2-boronic acid and 2-bromonitrobenzene, and benzothiophene-2-boronic acid and 2-bromonitrobenzene, respectively.

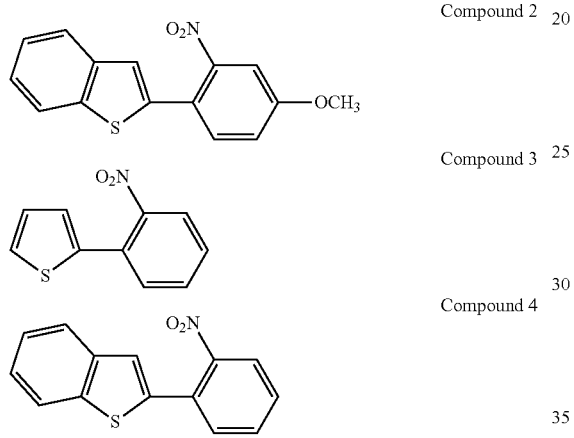

Compound 2

Compound 3

Compound 4

Example 2

Preparation of Compound 5

The following compound is prepared:

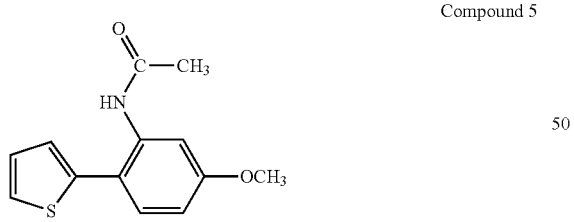

Compound 5

Compound 1 (75 mmol) is dissolved in 1:1 THF/methanol (160 mL). To the solution is added Zn dust (1.3 moles), followed by the dropwise addition of concentrate hydrochloric acid until analysis by thin layer chromatography (TLC) showed that Compound 1 and the reduction intermediates are completely consumed. Excess Zn is removed by filtration and washed with THF. The combined filtrates are concentrated in vacuo, and the residue is poured into water (1 L), and neutralized to pH=7-8 with 2 M NaOH. The resulting suspension is extracted with ethyl acetate. The organic phase is washed with brine, dried over anhydrous $Na_2SO_4$, and evaporated in vacuo to give the crude amino derivative.

The amino derivative is dissolved in THF (200 mL), and to the resulting solution is added $Ac_2O$ (20 mL) and pyridine (20 mL) at room temperature. The reaction mixture is stirred at room temperature for 5-6 h, and then heated at reflux for 1-2 h. The mixture is concentrated to an oil, which is then redissolved in ethyl acetate (500 mL) and washed with 5% HCl and brine respectively. The ethyl acetate solution is dried over anhydrous $Na_2SO_4$, concentrated and loaded on a silica gel column, which is eluted with a gradient of hexanes/ethyl acetate to give Compound 5 (16.2 g).

Example 3

Preparation of Compound 6

The following compound is prepared:

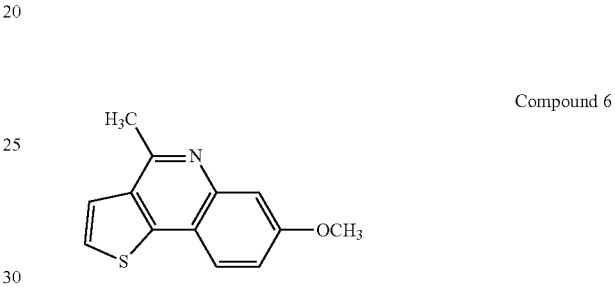

Compound 6

Compound 5 (65.6 mmol) is put in a dry flask (150 mL). To the flask is carefully added $POCl_3$ (80 mL). The mixture is stirred and heated at 80° C. for 30 min. The solution is concentrated in vacuo, and the residue is diluted with chloroform (500 mL). The chloroform solution is washed with ice/water (250 mL) and 5% ammonia (250 mL), then dried over anhydrous $Na_2SO_4$, and evaporated to afford a brown crude product. The crude product is further purified on a silica gel column using chloroform as the eluant to yield Compound 6 (10.2 g).

Example 4

Preparation of Compound 7

The following compound is prepared:

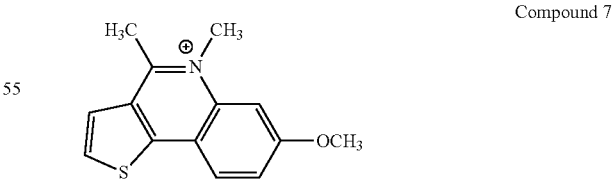

Compound 7

To a solution of Compound 6 (44.5 mmol) in chlorobenzene (150 mL), is added p-TsOMe (237 mmol), and the resulting mixture is heated at reflux for 2 days. The reaction mixture is then cooled to room temperature, and the resulting precipitate is collected by filtration. The resulting crude product is purified by recrystallization from ethyl acetate to give Compound 7 (10.5 g).

Example 5

Preparation of Compound 8

The following compound is prepared:

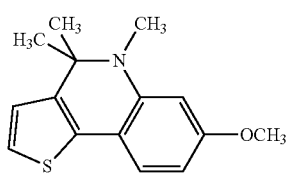

Compound 8

A solution is prepared of Compound 7 (7.2 mmol) in dry THF (50 mL) at 0° C. under $N_2$ gas. To the solution is slowly added MeMgCl (30 mmol) in THF. The reaction mixture is slowly warmed to room temperature and stirred for 2 days. The suspension is carefully poured onto crushed ice and acidified to pH=2 with 2 M HCl. The solution is then extracted with ethyl acetate, washed with brine and dried over anhydrous $Na_2SO_4$. The solution is concentrated in vacuo and purified on a silica gel column using 5:1 hexanes/ethyl acetate as the eluant to give Compound 8 (600 mg).

Example 6

Preparation of Compound 9

The following compound is prepared:

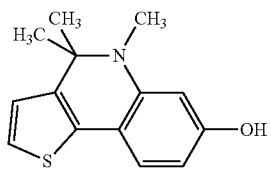

Compound 9

To a solution of Compound 8 (1.25 mmol) in dry $CH_2Cl_2$ (20 mL) is added $BBr_3$ (0.6 mmol) at 0° C., and the mixture is stirred at room temperature for 1 h. The reaction mixture is concentrated in vacuo, and cooled in a dry ice/acetone bath. To the residue is slowly added methanol (10 mL) to quench the residual $BBr_3$, followed by the addition of 100 mL water. The solution is neutralized to pH=7-8 with saturated $NaHCO_3$, extracted with ethyl acetate and washed with brine. The ethyl acetate solution is dried over anhydrous $Na_2SO_4$ and concentrated. The resulting residue is purified on a silica gel column using a gradient of hexanes/ethyl acetate as eluant to give Compound 9 (280 mg).

Example 7

Preparation of Compounds 10-12

The following compounds are prepared:

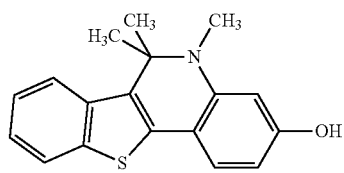

Compound 10

Compound 10 is prepared from Compound 2 following the procedures of Examples 2-6.

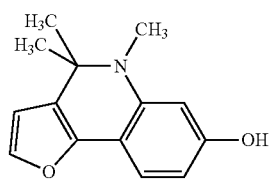

Compound 11

Compound 11 is prepared from furan-2-boronic acid following the procedures of Examples 1-6.

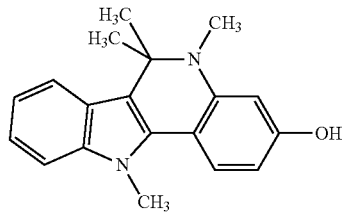

Compound 12

Compound 12 is prepared from N-methylindole-2-boronic acid following the procedures of Examples 1-6.

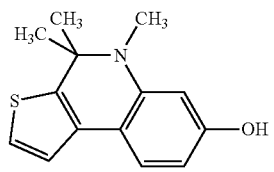

Compound 60

Compound 60 is prepared from thiophene-3-boronic acid following the procedures of Examples 1-6.

Compound 61

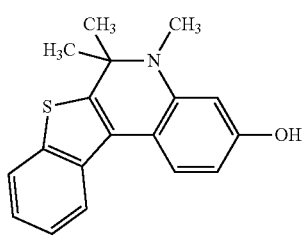

Compound 61 is prepared from benzothiophene-3-boronic acid following the procedures of Examples 1-6.

Example 8

Preparation of Compound 13

The following compound is prepared:

Compound 13

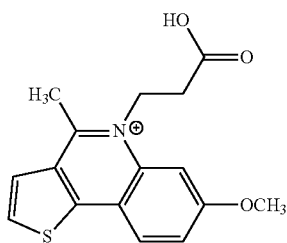

To a solution of Compound 6 (10 mmol) in chlorobenzene (50 mL), is added β-propiolactone (20 mmol). The solution is heated at reflux for 2 days, then cooled to room temperature, and the resulting precipitate collected by filtration. The crude product is purified by recrystallization from ethyl acetate to give Compound 13 (1.2 g).

Example 9

Preparation of Compound 14

The following compound is prepared:

Compound 14

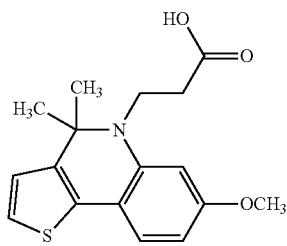

Compound 13 is treated with MeMgCl to give Compound 14, following the procedure of Example 5.

Example 10

Preparation of Compound 15

The following compound is prepared:

Compound 15

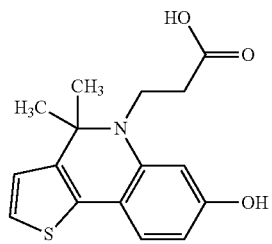

Compound 14 is treated with $BBr_3$ to give Compound 15, following the procedure of Example 6.

Example 11

Preparation of Compound 16

The following compound is prepared:

Compound 16

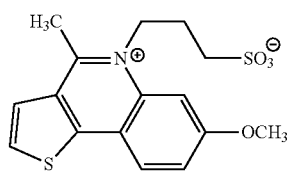

To a solution of Compound 6 (20 mmol) in chlorobenzene (80 mL), is added 1,3-propanesultone (30 mmol), and the reaction mixture is heated at reflux for 3 days. After cooling to room temperature, the reaction mixture is filtered and the precipitate collected. The crude material is washed with chloroform and recrystallized from isopropyl alcohol to give Compound 16 (1.4 g).

Example 12

Preparation of Compound 17

The following compound is prepared:

Compound 17

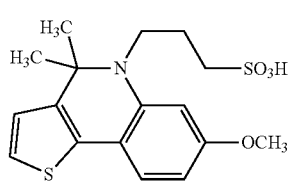

Compound 16 is treated with MeMgCl to give Compound 17, following the procedure of Example 5.

Example 13

Preparation of Compound 18

The following compound is prepared:

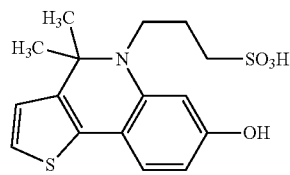

Compound 18

Compound 16 is treated with BBr$_3$ to give Compound 18, following the procedure of Example 6.

Example 14

Preparation of Compound 19

The following compound is prepared:

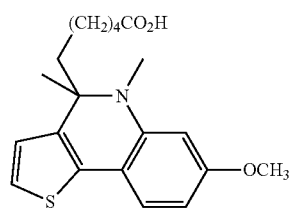

Compound 19

To a solution of Compound 7 (6 mmol) in dry THF (100 mL) is slowly added 6-(2,4,10-trioxatricyclo[3.3.1.1]dec-3-yl)hexylmagnesium bromide (50 mmol) in THF at 0° C. under N$_2$ gas. The reaction mixture is slowly warmed to room temperature, and stirred for 2 days. The suspension is carefully poured onto crushed ice, and acidified to pH=2 with 2 M HCl. The solution is extracted with ethyl acetate, and evaporated in vacuo to dryness. The residue is redissolved in methanol (25 mL), 5 M HCl (10 mmol) is added, and the solution is stirred at room temperature overnight. The reaction mixture is concentrated in vacuo, poured into water, and extracted with ethyl acetate. The combined organic layers are washed with brine, dried over anhydrous Na$_2$SO$_4$, and evaporated in vacuo to give a crude product, which is further purified by chromatography on silica gel using 4:1 chloroform/methanol as the eluant to give Compound 19 (615 mg).

Example 15

Preparation of Compound 20

The following compound is prepared:

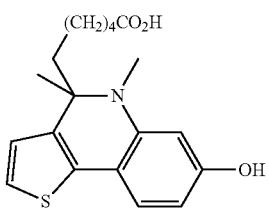

Compound 20

Compound 19 is treated with BBr$_3$ to give Compound 20, following the procedure of Example 6.

Example 16

Preparation of Compound 21

The following compound is prepared:

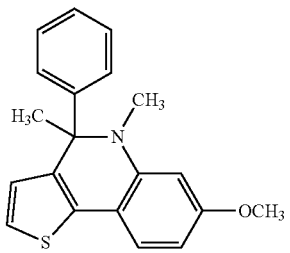

Compound 21

To a solution of Compound 7 (7.2 mmol) in dry THF (50 mL) is slowly added PhMgCl (30 mmol) in THF at 0° C. under N$_2$ gas. The reaction mixture is slowly warmed to room temperature, and stirred for 2 days. The resulting suspension is carefully poured onto crushed ice, acidified to pH=2 with 2 M HCl, extracted with ethyl acetate, washed with brine and dried over anhydrous Na$_2$SO$_4$. The solution is then concentrated in vacuo and the residue is purified by chromatography on silica gel using 5:1 hexanes/ethyl acetate as eluant to give Compound 21 (656 mg).

Example 17

Preparation of Compound 22

The following compound is prepared:

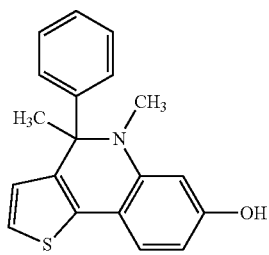

Compound 22

Compound 21 is treated with BBr$_3$ to give Compound 22, following the procedure of Example 6.

Example 18

Preparation of Compounds 23-36

The following general method is utilized to prepare Compounds 23-36. A derivatized 3-aminophenol (2 mmol) and a 2-sulfobenzaldehyde precursor (1 mmol) are dissolved in DMF. To the DMF solution is slowly added trifluoroacetic acid (TFA, 1 ml) at room temperature. The reaction mixture is stirred overnight, then heated to 110-120° C. for 7-10 h. The mixture is concentrated in vacuo, the residue is dissolved in a minimal amount of chloroform, and purified by chromatography on silica gel to yield the desired product.

TABLE 4

| 3-aminophenol precursor | 2-sulfobenzaldehyde precursor | Product |
| --- | --- | --- |
| Compound 9 | | Compound 23 |
| Compound 10 | | Compound 24 |
| Compound 10 | | Compound 25 |

TABLE 4-continued
| 3-aminophenol precursor | 2-sulfobenzaldehyde precursor | Product |
| --- | --- | --- |
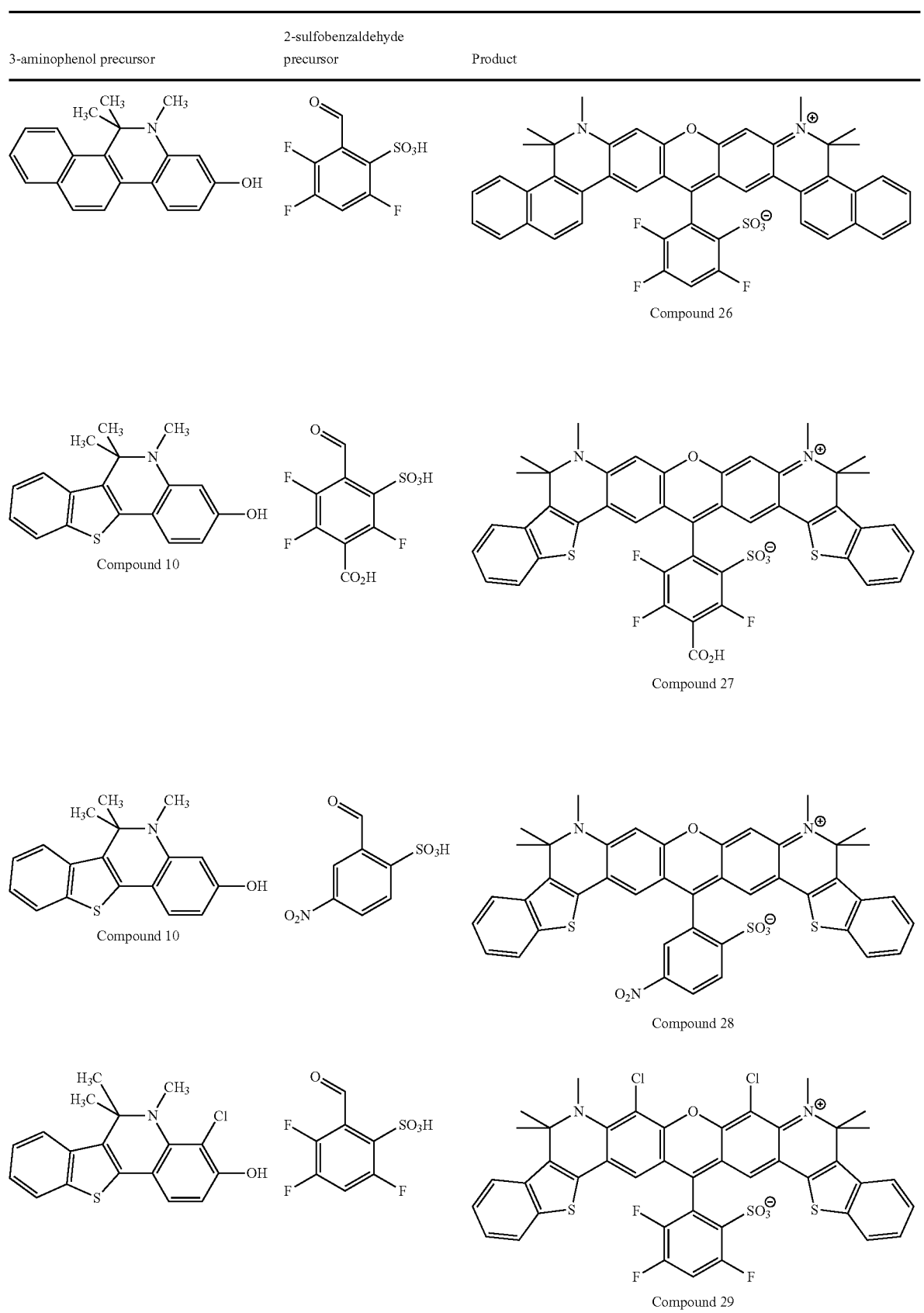
Compound 26
Compound 10
Compound 27
Compound 10
Compound 28
Compound 29

TABLE 4-continued
| 3-aminophenol precursor | 2-sulfobenzaldehyde precursor | Product |
|---|---|---|
| 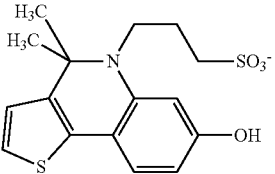<br>Compound 18 | 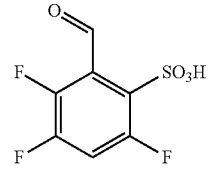 | 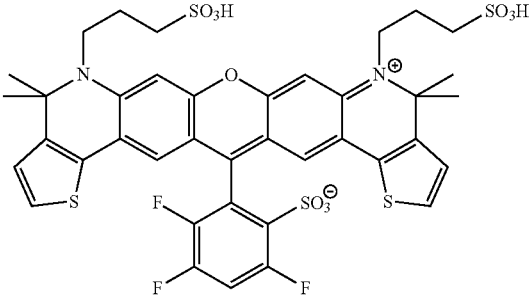<br>Compound 30 |
| 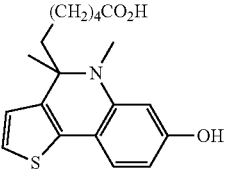<br>Compound 20 |  | 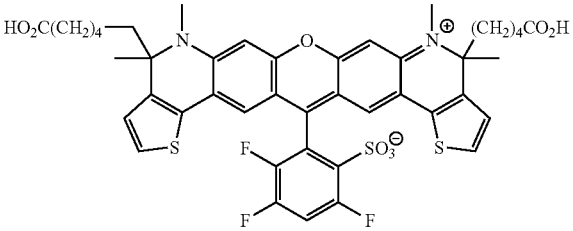<br>Compound 31 |
| 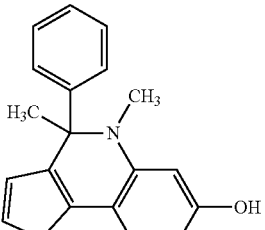<br>Compound 22 | 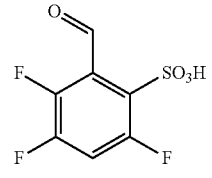 | 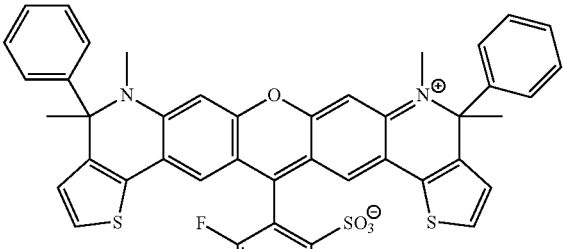<br>Compound 32 |
| 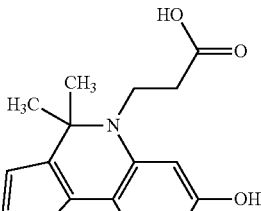<br>Compound 15 | 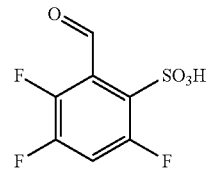 | 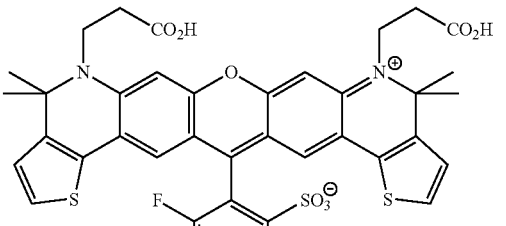<br>Compound 33 |

TABLE 4-continued

| 3-aminophenol precursor | 2-sulfobenzaldehyde precursor | Product |
|---|---|---|
| Compound 18 | | Compound 34 |
| Compound 11 | | Compound 35 |
| Compound 12 | | Compound 36 |
| Compound 60 | | Compound 62 |

Example 19

Preparation of Compound 37

The following compound is prepared:

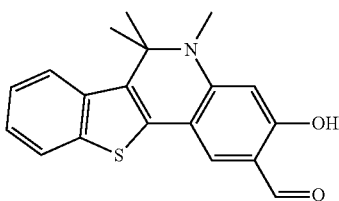

Compound 37

POCl$_3$ (0.3 mL) is dissolved in dry DMF (8 mL) at 0° C., and the mixture is stirred at room temperature for 0.5 h. To the reaction mixture is added Compound 10 (2 mmol) in DMF (2 mL). The resulting solution is carefully poured into cold 10% NaHCO$_3$, and extracted with ethyl acetate. The combined organic layers are washed with brine and dried over anhydrous Na$_2$SO$_4$. The solution is evaporated in vacuo to give Compound 37 (516 mg).

Example 20

Preparation of Compound 38

The following compound is prepared:

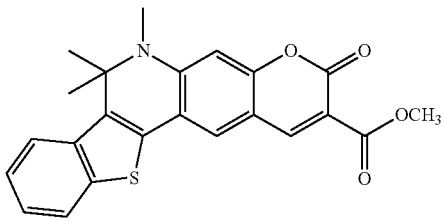

Compound 38

To a solution of Compound 37 (2 mmol) and dimethylmalonate (2.5 mmol) in methanol (10 mL) is added piperidine (0.1 mL). The reaction mixture is heated at reflux for 7 h, and concentrated in vacuo. The resulting residue is poured into water, and extracted with ethyl acetate. The combined organic layers are washed with brine and dried over anhydrous Na$_2$SO$_4$. The solution is evaporated under vacuum, and the resulting crude material is purified by chromatography on silica gel using 50:1 chloroform/methanol as the eluant to give Compound 38 (256 mg).

Example 21

Preparation of Compound 39

The following compound is prepared:

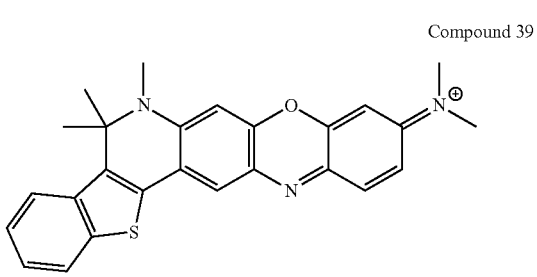

Compound 39

A solution of Compound 10 (1 mmol) and N,N-dimethyl-3-hydroxy-4-nitrosoaniline (1.6 mmol) in 1:1 butanol/toluene (10 mL) is heated at reflux for 16 h with a Dean-Stark trap. The reaction mixture is concentrated in vacuo, and the residue is poured into water and extracted with ethyl acetate. The combined organic layers are washed with brine and dried over anhydrous Na$_2$SO$_4$. The organic solution is evaporated under vacuum, and the resulting crude material is purified by chromatography on silica gel eluting with 5:1 chloroform/methanol to give Compound 39 (56 mg).

Example 22

Preparation of Compound 40

The following compound is prepared:

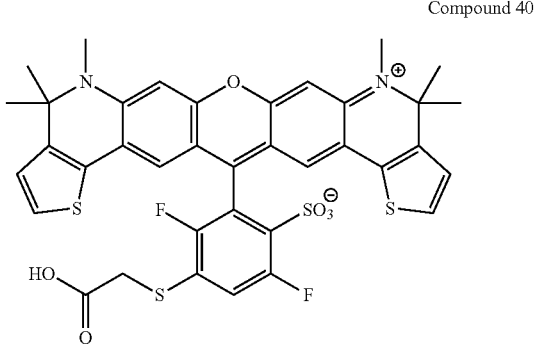

Compound 40

To a solution of Compound 23 (0.14 mmol) in dimethylacetamide (60 mL) is added thioacetic acid (1.5 mL) at room temperature. The reaction mixture is heated at 110-120° C. for 2 h, then cooled to room temperature and poured into water. The suspension is extracted with chloroform, washed with water, and the chloroform extract is dried over anhydrous Na$_2$SO$_4$ and concentrated in vacuo. The residue is purified on a silica gel column using 20:1, 10:1, 5:1 chloroform/methanol and 3:1:0.01 chloroform/methanol/acetic acid as the eluants to give Compound 40 (90 mg).

Compound 62 (Example 18) is treated with thioacetic acid according to the above procedure to yield the analogous 6-carboxymethylthio derivative, Compound 63.

Example 23

Preparation of Compound 41

The following compound is prepared:

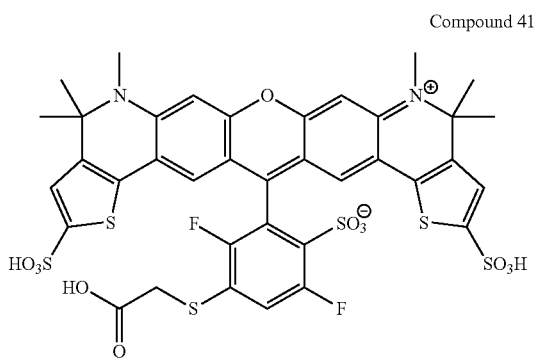

Compound 41

To a solution of Compound 40 (0.12 mmol) in 98% sulfuric acid (5 mL) is slowly added 30% fuming sulfuric acid (4 mL) at 0° C. The reaction mixture is stirred for 10 min at 0° C., and poured into cold ether. The resulting precipitate is collected, washed with ether, and redissolved in methanol. The methanol solution is neutralized to pH=7-8 with saturated $Li_2CO_3$, and the resulting white precipitate ($Li_2SO_4$) is removed by filtration and washed with methanol. The filtrate is concentrated and purified by HPLC to give Compound 41 (60 mg).

The fluorescence quantum yield of Compound 41 is determined using sulforhodamine 101 (in ethyl alcohol) as the reference standard ($\Phi_F$=0.90). The concentrations of sulforhodamine 101 (the reference) and Compound 41 are adjusted to obtain an absorbance of 0.25 (in 1 cm cell) at 560 nm. The sample and reference are each excited at 560 nm and their fluorescence spectra obtained. The fluorescence quantum yield of the sample ($\Phi_F^X$) in the indicated solvent was calculated from the following formula, considering that the peak area ($A_R$) of the emission spectrum of the reference and that of the tested dye ($A_x$) can be readily determined:

$$\Phi F^X = A_x \Phi_F^R A_R$$

where $\Phi_F^R$ and $\Phi_F^X$ are the fluorescence quantum yields of the reference and the testing dye. The measurements are done in triplicate and the estimated errors are no more than 1%. The quantum yields of Compound 41 are determined to be 0.72 (in methyl alcohol) and 0.68 (in water) respectively.

Compound 63 is sulfonated using the above procedure to yield the analogous disulfonate derivative, Compound 64.

Example 24

Preparation of Compound 42

The following compound is prepared:

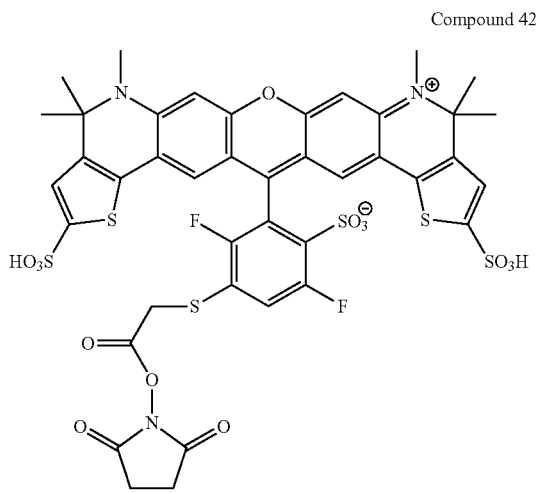

Compound 42

To a solution of Compound 41 (0.019 mmol) in dry DMF (10 mL) is added N,N' disuccinimidylcarbonate (0.23 mmol) and 4-dimethylaminopyridine (0.04 mmol) at room temperature, and the mixture is stirred for 6 h. The solution is then concentrated in vacuo, and the residue is suspended in ethyl acetate (100 mL). The precipitate is collected and washed with ethyl acetate. The crude solid is redissolved in dry DMF, ethyl acetate (100 mL) is added, and the resulting precipitate is collected, washed with ethyl acetate, and dried to give Compound 42 (20 mg).

Example 25

Preparation of Compound 43

The following compound is prepared:

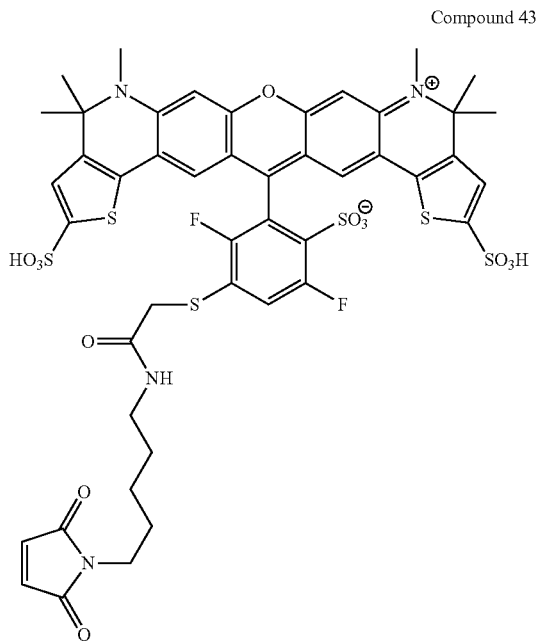

Compound 43

To a solution of Compound 42 (0.1 mmol) in anhydrous DMF (2 mL) is slowly added 1 mL DMF solution of N-(5-aminopentyl)maleimide (0.12 mmol). To the reaction mixture is then added triethylamine (0.15 mmol), and the resulting mixture is stirred at room temperature for 5-8 h. The solution is then concentrated under vacuum and poured into ethyl acetate. The resulting precipitate is collected by filtration, and washed with ethyl acetate. The crude product is purified by HPLC to give Compound 43 (26 mg).

Example 26

Preparation of Compound 44

The following compound is prepared:

Compound 44

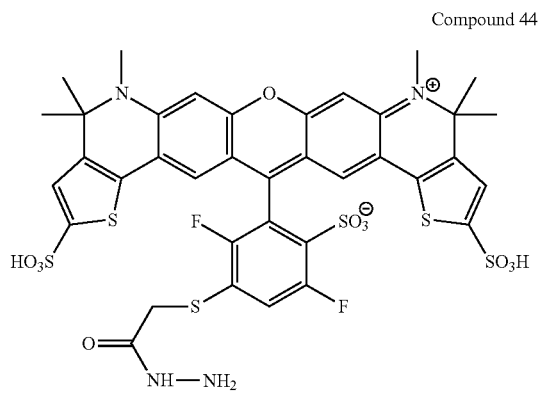

To a solution of hydrazine (0.5 mmol) in DMF (0.05 mL) is slowly added 2 mL DMF solution of Compound 42 (0.1 mmol). The resulting mixture is stirred at room temperature for 5-8 h. The reaction solution is then concentrated under vacuum and poured into isopropyl alcohol. The resulting precipitate is collected by filtration, and washed with isopropyl alcohol. The crude material is purified by HPLC to give Compound 44 (39 mg).

Example 27

Preparation of Compound 45

The following compound is prepared:

Compound 45

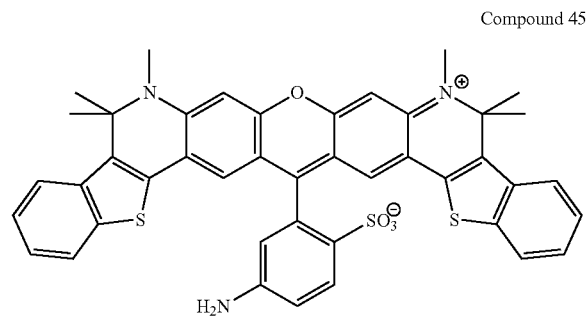

Compound 28 (1 mmol) is dissolved in 10:1 methanol/water (60 mL). To the resulting solution is added $Na_2S$ (1.5 moles) and NaSH (4.5 mmol). The reaction mixture is heated at reflux for 1.5 h, then concentrated in vacuo. The residue is poured into water (250 mL) and neutralized to pH=7-8 with 2 M HCl. The resulting suspension is extracted with chloroform, the organic phase is washed with brine, dried over anhydrous $Na_2SO_4$, and evaporated in vacuo. The resulting crude product is further purified by chromatography on silica gel, eluting with a gradient of chloroform/methanol to give Compound 45.

Example 28

Preparation of Compound 46

The following compound is prepared:

Compound 46

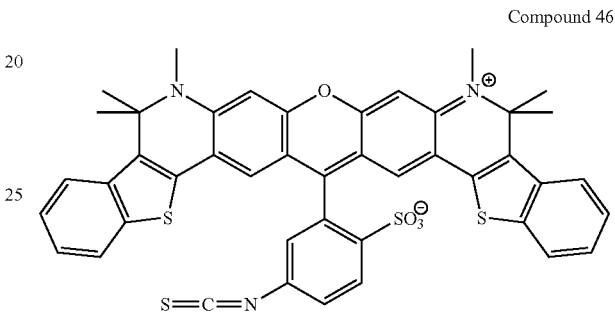

Compound 45 (0.1 mmol) is dissolved in dry DMF (10 mL) and thiophosgene (1 mmol) is added. The reaction mixture is stirred at room temperature for 6 h, concentrated in vacuo, and poured into ether. The resulting precipitate is collected, and washed with ether to give Compound 46 (45 mg).

Example 29

Preparation of Compound 47

The following compound is prepared:

Compound 47

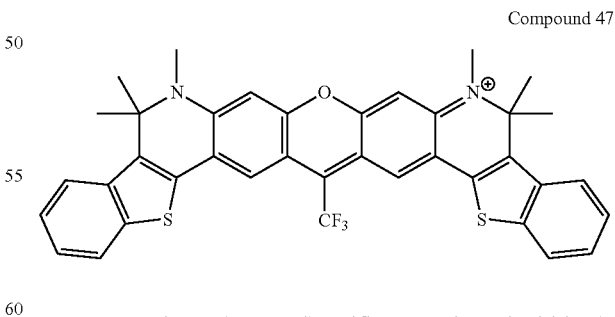

Compound 10 (1 mmol), trifluoroacetic anhydride (5 mmol) and TFA (1.5 mmol) are dissolved in $CH_2Cl_2$ (2.5 mL). The reaction mixture is stirred for 2 days, then concentrated in vacuo, and redissolved in ethanol (1 mL) containing 70% perchloric acid (0.1 g). The precipitate is collected, and purified on a silica gel column using 10:1 chloroform/methanol to afford Compound 47 (128 mg).

Example 30

Preparation of Compound 48

The following compound is prepared:

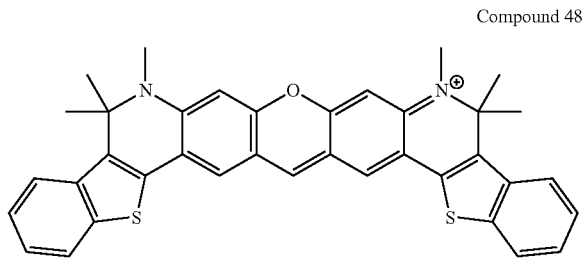

Compound 48

To a solution of Compound 10 (5 mmol) in ethanol (20 mL) is added 37% formaldehyde (20 mmol) at room temperature, and the mixture is stirred at room temperature for 2 days. The resulting yellow solid is collected and dried. To the solution of the crude solid in concentrated sulfuric acid (5 mL) is slowly added 1 M $NaNO_2$ at 0° C. The solution is allowed to stand at room temperature for 2 days, and the precipitate is collected. The crude solid is purified by chromatography on silica gel using a gradient of chloroform/methanol to give Compound 48 (28 mg).

Example 31

Preparation of Compound 49

The following compound is prepared:

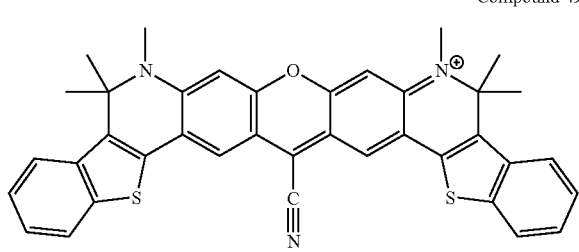

Compound 49

To a solution of Compound 48 (0.5 mmol) in DMF (20 mL) is added KCN (20 mmol) at room temperature, and the mixture is stirred at room temperature for 2 days. Oxygen gas is bubbled through the solution for 6 h. The solution is concentrated in vacuo, and purified by chromatography on silica gel, eluting with a gradient of chloroform/methanol to give Compound 49 (31 mg).

Example 32

Preparation of Compound 50

The following compound is prepared:

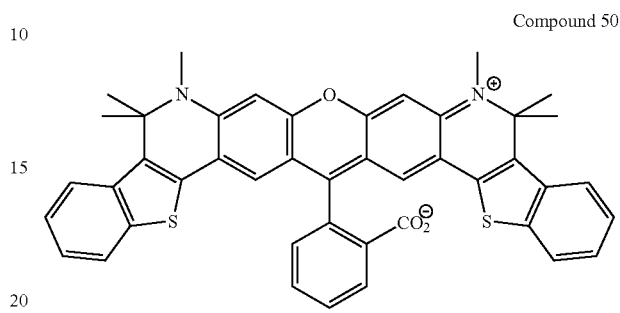

Compound 50

To a suspension of Compound 10 (1 mmol) and phthalic anhydride (0.4 mmol) in propionic acid (10 mL) is slowly added 98% sulfuric acid (0.1 mL). The reaction mixture is heated at 130-140° C. for 6 h, then carefully poured onto crushed ice, and extracted with ethyl acetate. The combined organic layers are washed with brine and dried over anhydrous $Na_2SO_4$. The solution is concentrated in vacuo and purified by chromatography on silica gelusing 5:1 chloroform/methanol as the eluant to give Compound 50 (356 mg).

Example 33

Preparation of Compound 51

The following compound is prepared:

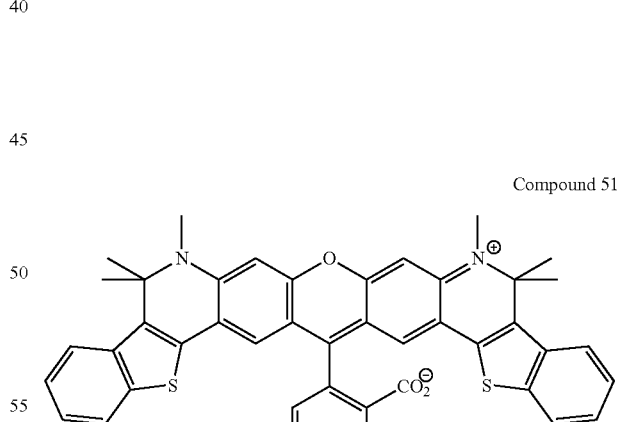

Compound 51

The reaction of Compound 10 (1 mmol) with compound pyridine-3,4-dicarboxylic anhydride (0.4 mmol) in propionic acid (10 mL) produces Compound 51 analogously with the procedure used to prepare Compound 50.

Example 34

Preparation of Compound 53

The following compound is prepared:

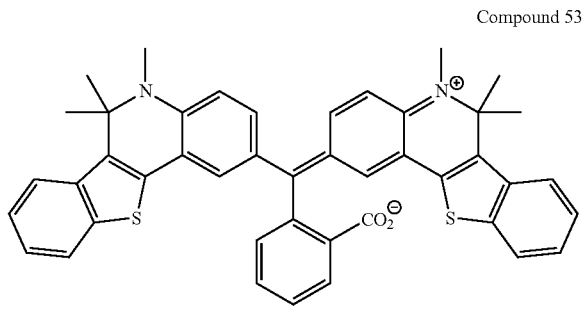

Compound 53

N-methyl-2,2-dimethyl-1,2-dihydrothianaphtheno[3,4]quinoline (Compound 52) is prepared from Compound 4 using the procedures of Examples 2-5. Compound 52 (1 mmol) and phthalic anhydride (0.45) are mixed well, and melted for 15 minutes in vacuo. The mixture is then cooled to room temperature, and extracted with methanol (50 mL). The methanol solution is evaporated under vacuum, and the resulting crude solid is purified by chromatography on silica gel eluting with 10:1:1 chloroform/methanol/ethyl acetate to give Compound 53 (156 mg).

Example 35

Preparation of Compound 54

The following compound is prepared:

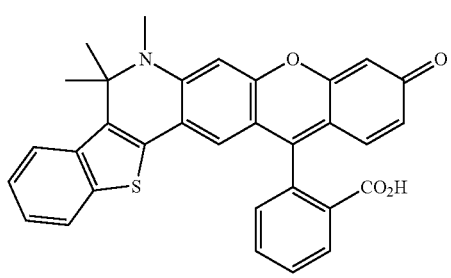

Compound 54

To a solution of Compound 10 (1 mmol) in methanesulfonic acid (5 mL) is slowly added 2-(2,4-dihydroxybenzoyl)benzoic acid (1.1 mmol). The reaction mixture is heated at 50-60° C. for 2 h. The solution is then carefully poured onto crushed ice, and extracted with ethyl acetate. The combined organic layers are washed with brine and dried over anhydrous $Na_2SO_4$. The solution is concentrated in vacuo and purified by chromatography on silica gel using 5:1 chloroform/methanol as the eluant to give Compound 54 (96 mg).

Example 36

Preparation of Compound 55

The following compound is prepared:

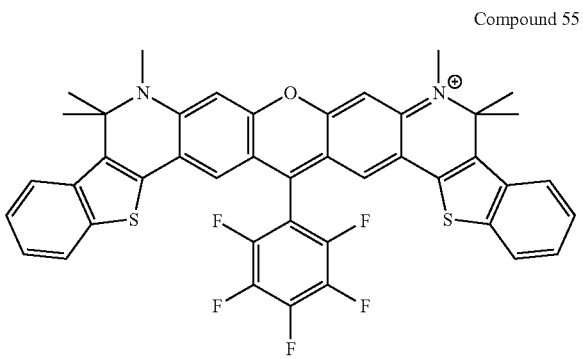

Compound 55

To a solution of Compound 10 (1 mmol) and pentafluorobenzaldehyde (0.4 mmol) in propionic acid (10 mL) is slowly added p-TsOH (25 mg). The reaction mixture is heated at 130-140° C. for 6 h, cooled to room temperature, and poured into water. The resulting solution is extracted with ethyl acetate, and the combined organic layers are washed with brine, dried over anhydrous $Na_2SO_4$, and evaporated under vacuum. The resulting crude material is purified by chromatography on silica gel eluting with 10:1 chloroform/methanol to give Compound 55 (156 mg).

Example 37

Preparation of Compound 56

The following compound is prepared:

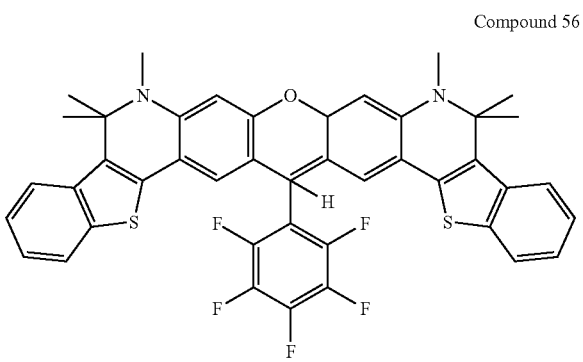

Compound 56

To a solution of Compound 55 (0.1 mmol) and in ethanol (5 mL) is slowly added $NaBH_4$ (5 mmol) at 0° C. The reaction mixture is warmed to room temperature, stirred for 2 h, and poured into ice/water. The resulting suspension is extracted with ethyl acetate, and the combined organic layers are washed with brine, dried over anhydrous $Na_2SO_4$, and evaporated under vacuum. The resulting crude material is purified by chromatography on silica gel using 10:1 chloroform/ethyl acetate as the eluant to give Compound 56 (35 mg).

Example 38

Preparation of Compound 57

The following compound is prepared:

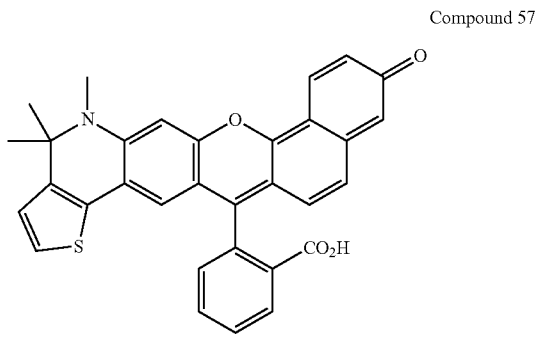

Compound 57

To a solution of 2-(2'-carboxybenzoyl)-1,6-dihydroxynaphthalene (1 mmol) in methanesulfonic acid (5 mL) is slowly added Compound 9 (1.1 mmol). The reaction mixture is heated at 50-60° C. for 2 h, the solution is carefully poured onto crushed ice, and extracted with ethyl acetate. The combined organic layers are washed with brine, dried over anhydrous $Na_2SO_4$, and concentrated under vacuum. The resulting residue is purified by chromatography on silica gel using 5:1 chloroform/methanol as eluant to give Compound 57 (76 mg).

Example 39

Preparation of Compound 58

The following compound is prepared:

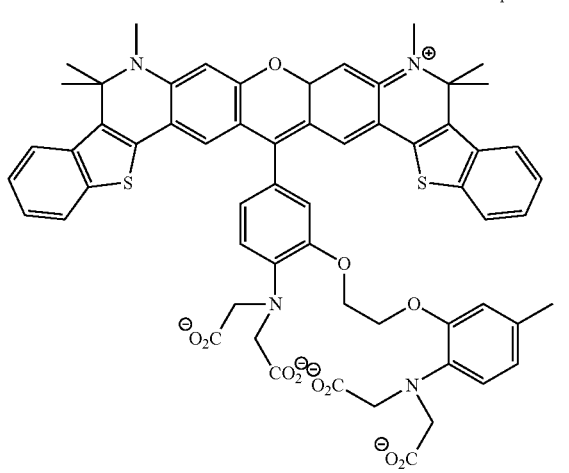

Compound 58

Compound 10 (0.15 g, 0.51 mmol), 1-(2-bis(methoxycarbonylmethyl)amino-5-methyl)-2-(2-bis(methoxycarbonylmethyl)amino-5-formylphenoxy)ethane (0.146 g, 0.25 mmol), and catalytic p-TsOH are suspended in propionic acid (10 mL) under nitrogen atmosphere and sparged with nitrogen for 40 minutes while being heated to 60° C. The reaction mixture is heated overnight. After cooling, the solution is poured into a solution of 11 g sodium acetate in 100 mL water with stirring. The resulting precipitate is collected by suction filtration, rinsed with water, and dried in vacuo to give 0.28 g of a pale green powder.

The intermediate (0.28 g; 0.25 mmol) is dissolved in methanol/chloroform (1:1, 12 mL) and treated with p-chloranil (0.123 g, 0.50 mmol). The resulting mixture is stirred at room temperature until TLC analysis shows consumption of starting material (approximately 1.5 hours). The reaction mixture is suction filtered and the filtrate concentrated in vacuo. The resulting dark blue residue is purified by flash chromatography on 35 g siliga gel using chloroform:methanol:acetic acid (50:5:1) as eluant. Pure product fractions are combined and concentrated in vacuo to give 52 mg of a dark blue solid.

All of the blue intermediate is converted to the free carboxylic acid form by treatment of 52 mg (40 mmol) with 1 M KOH (0.35 mL, 0.35 mmol) in dioxane/methanol (5:3 mL). The resulting dark amber mixture is stirred at room temperature overnight, then concentrated in vacuo. The residue is suspended in 5 mL water, and the pH (13) is adjusted to 2 by the addition of aqueous HCl. The resulting blue precipitate is collected by filtration, rinsed with water, and dried under vacuum to yield 45 mg of a dark blue powder. The product is further purified dissolution in dilute aqueous KOH solution, followed by chromatography on SEPHADEX LH-20 resin using water as eluant. Pure product fractions are combined and lyophilized to give Compound 58 as a dark blue powder, $R_f$=0.45 (dioxane:isopropyl alcohol:water:ammonium hydroxide 15:58:13:13)).

Example 40

Determination of the $Ca^{2+}$ Binding Affinity of Compound 58

The fluorescence response and dissociation constant of Compound 58 is determined using the method described by Tsien et al. METH. ENZYM. 172, 230 (1989). Compound 58 (1 mg) is dissolved in deionized water and 5 L of this solution is diluted into 3 mL of each of two buffers, which are cross diluted to arrive at a series of $Ca^{2+}$ concentrations between zero and 35 M. Emission spectra of the dye solutions are scanned between dilutions to generate a family of curves. Each of these curves has maximal fluorescence emission at approximately 640 nm with an increase in fluorescence emission intensity with increasing $Ca^{2+}$ concentration. This intensity change is plotted against the concentration of free $Ca^{2+}$ to give a value for the dissociation constant of the indicator. The calculated dissociation constant at 20° C. is 57.5 μM.

Example 41

Preparation of Compound 59

The following compound is prepared:

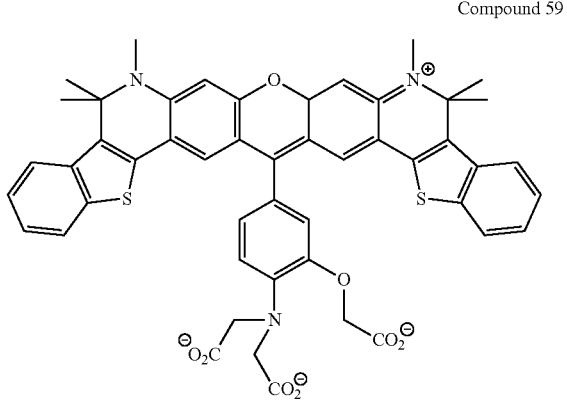

Compound 59

A light green mixture of 2-carboxymethoxy-4-formyl-aniline-N,N-diacetic acid, trimethyl ester (4-formyl APTRA, trimethyl ester; 60 mg, 0.17 mmol), Compound 10 (0.10 g, 0.34 mmol) and catalytic p-TsOH in 8 mL propionic acid is degassed in vacuo, flushed with nitrogen gas three times, then heated to 75 degrees with stirring in darkness overnight. After cooling, the reaction solution is poured into a solution of 10 g sodium acetate in 100 mL water. The resulting precipitate is collected by suction filtration, rinsed with water, and dried in vacuo to give 0.15 g of a green powder (100%, $R_f$ 0.30 (EtOAc/hexanes)). All of this powder (0.17 mmol) is dissolved in 1:1 methanol:chloroform (10 mL), and p-chloranil (50 mg, 0.20 mmol) is added. The resulting mixture is stirred for 3 hours, then concentrated in vacuo. The residue is purified by preparative silica gel TLC, using chloroform:methanol:acetic acid (50:5:1) as eluant. The desired product band ($R_f$ 0.20) is scraped from the plate. The product is extracted from the silica gel using chloroform:methanol:acetic acid (50:5:1), followed by filtration and concentration in vacuo to give 49 mg (31%) of a dark blue powder. This powder (40 mg, 0.041 mmol) is dissolved in 4 mL methanol and 1M KOH solution (0.26 mL, 0.26 mmol) is added. After stirring overnight, TLC shows product formation ($R_f$ 0.15 (dioxane:isopropyl alcohol:water:ammonium hydroxide 15:58:13:13)) and starting material consumption ($R_f$ 0.75). The reaction solution is added to 30 mL aqueous citric acid (pH 2). The resulting precipitate is collected on a Hirsch funnel, rinsed with water, and dried in vacuo to give Compound 59 as 25 mg of a blue powder.

Example 42

Preparation of a Tyramine Conjugate

The following compound is prepared:

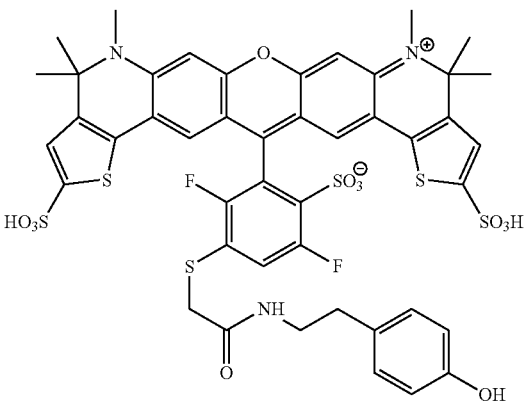

To a solution of Compound 42 (0.1 mmol) (Example 25) in anhydrous DMF (2 mL) is slowly added 1 mL DMF solution of tyramine (0.22 mmol). The resulted mixture is stirred at room temperature for 5-8 h until the dye is completely consumed. The reaction solution is concentrated in vacuo, and poured into ethyl acetate. The resulting precipitate is collected by filtration and washed with ethyl acetate. The crude material is further purified by HPLC to give the desired product.

Example 43

Labeling of Mitochondria in Live Cells

The NIH/3T3 mouse fibroblast cell line is obtained from American Type Culture Collection Co., Rockville, Md. The cells are maintained in a humidified atmosphere of 5% $CO_2$ in Dulbecco's modified Eagle's medium (DMEM) supplemented with 10% calf serum, 50 μg/mL gentamicin, 300 μg/mL L-glutamine and 10 mM HEPES pH 7.4. Cells are subcultured every 3 days by trypsinization using 0.05% trypsin and 0.02% EDTA in a Ca- and Mg-free saline solution (Gibco BRL, Gaithersburg, Md.). Cell passage number ranges from 120-122. To obtain well-spread single cells, $5 \times 10^4$ cells are plated onto 18×18 mm coverslips in 60 mm culture dishes.

A cationic dye, such as Compound 48, 49 or 55, is dissolved in DMSO/ethanol (1/1) to prepare a 5 mM stock solution. The stock solutions are kept sealed in an amber reagent bottle and stored at 4° C. Each labeling medium is prepared by adding stock solution to fresh culture medium in an amount sufficient to make final dye concentrations of between 50 and 200 nM.

The 3T3 cells are transferred to the labeling medium containing the selected dye and incubated at 37° C. for 15 to 30 minutes. The cells are then washed with fresh medium and observed using a Zeiss Axioplan microscope equipped with a filter optimized for tetramethylrhodamine. The selected dyes stain mitochondria selectively and fluorescently.

Example 44 pH Titration of Compound 57

Figure 3:
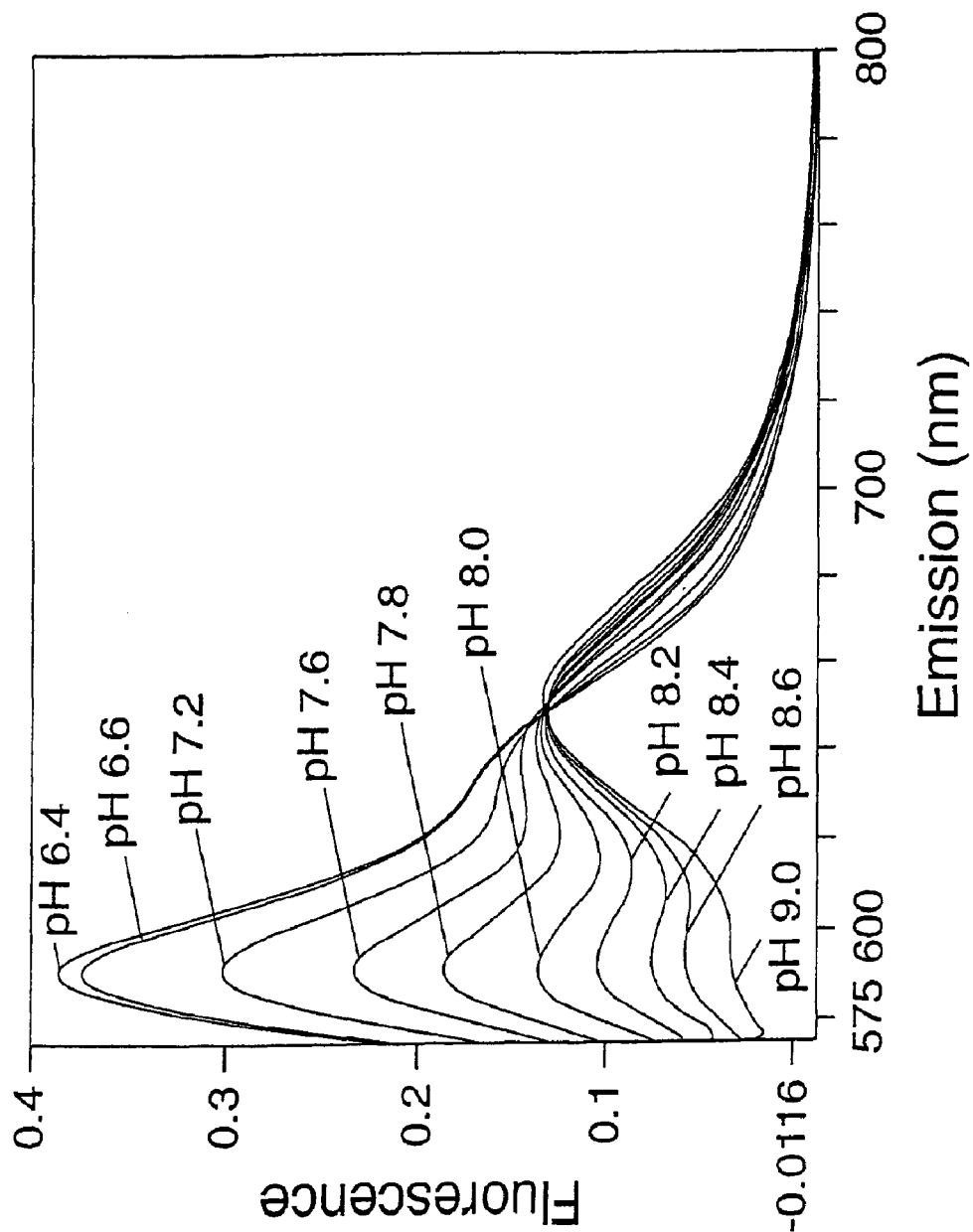
FIG. 3: The effect of pH on the fluorescence emission of Compound 57, as described in Example 44.

Compound 57 is first dissolved in a series of buffers that have each been calibrated using a pH meter. Acetate buffers are typically used in the range of pH 4-6, and phosphate buffers in the pH range 6-8. Absorption measurements are made using solutions that are approximately 10 M in concentration, and fluorescence measurements are made using solutions that are approximately 1 µM in concentration. The absorption or emission data is then plotted versus pH to determine pKa values. For example, FIG. 3 shows the fluorescence emission data for Compound 57 plotted versus the pH of the solution, when excited at 338 nm.

Example 45

Preparation of a Phalloidin Dye-Conjugate

To aminophalloidin p-toluenesulfonate (3.5 mg, 4 µmol) and Compound 42 (6.0 mg, 5 µmol) in DMF is added N,N-diisopropylethylamine (2 µL, 11 µmol). The mixture is stirred at room temperature for 3 hours. To this is added 7 mL of diethyl ether. The solid is collected by centrifugation. The crude product is purified on SEPHADEX LH-20, eluting with water to give the pure phalloidin conjugate.

Example 46

Preparation of a Drug Dye-Conjugate

A fluorescent dopamine $D_2$ antagonist is prepared as follows: To 10 mg of N-(p-aminophenethyl)spiperone (Amlaiky et al., FEBS LETT 176, 436 (1984)), and 10 µL N,N-diisopropylethylamine in 1 mL of DMF is added 15 mg of Compound 42. After 3 hours, the reaction mixture is poured into 5 mL ether. The precipitate is centrifuged, then purified by chromatography on silica gel using 10-30% methanol in chloroform.

Example 47

Preparation of Protein Dye-Conjugates

A series of dye conjugates of goat anti-mouse IgG, streptavidin and other proteins, including R-phycoerythrin (R-PE) are prepared by standard means (Haugland et al., METH. MOL. BIOL. 45, 205 (1995); Haugland, METH. MOL. BIOL. 45, 223 (1995); Haugland, METH. MOL. BIOL. 45, 235 (1995)) using Compound 42 and a succinimidyl ester derivative of CY-5 dye.

A solution of the desired protein is prepared at 10 mg/mL in 0.1 M sodium bicarbonate. The labeling reagents are dissolved in DMF at 10 mg/mL. Predetermined amounts of the labeling reagents are added to the protein solutions with stirring. A molar ratio of 10 equivalents of dye to 1 equivalent of protein is typical, though the optimal amount varies with the particular labeling reagent, the protein being labeled and the protein's concentration, and is determined empirically. The reaction mixture is incubated at room temperature for one hour, or on ice for several hours. The dye-protein conjugate is typically separated from free unreacted reagent by size-exclusion chromatography on BIO-RAD P-30 resin equilibrated with PBS. The initial, protein-containing colored band is collected and the degree of substitution is determined from the absorbance at the absorbance maximum of each fluorophore, using the extinction coefficient of the free fluorophore.

TABLE X

Fluorescence of Selected Protein Conjugates of the Invention

| Protein | DOS | Quantum Yield |
|---|---|---|
| Goat anti-Mouse IgG | 1.2 | 1.14 |
| Streptavidin | 3.60 | 0.98 |
| Wheat Germ Agglutinin | 1.13 | 0.56 |
| Conconavilin A | 1.10 | 0.43 |
| Goat anti-Rabbit IgG (highly absorbed) | 1.50 | 1.36 |
| Goat anti-Chicken IgG | 1.40 | 0.99 |
| Rabbit anti-Mouse IgG | 1.30 | 1.10 |
| Goat anti-Mouse IgG (highly absorbed) | 1.30 | 1.40 |
| Goat anti-Guinea Pig IgG | 1.20 | 1.40 |
| Protein A (MR = 4) | 2.20 | 1.44 |
| Protein A (MR = 8) | 4.40 | 0.68 |
| Transferrin (MR = 20) | 1.30 | 1.20 |

*Extinction coefficients are determined for the free carboxylic acid in aqueous solution Protein conjugates of antibody fragments, of other avidins and of other proteins are prepared and analyzed similarly.

Example 48

Fluorescent Labeling of Periodate-Oxidized Proteins

Two samples of 5 mg each of goat IgG antibody in 1 mL of 0.1 M acetate, 0.135 M NaCl, pH 5.5 are treated with 2.1 mg of sodium metaperiodate on ice, for 1 and 2 hours, respectively. The reactions are stopped by addition of 30 µL ethylene glycol. The antibodies are purified on a MATREX GH 25 column (1 cm×30 cm) packed in PBS pH 7.2. One-tenth volume of 1 M sodium bicarbonate is added to increase the pH and Compound 44 is added at a molar ratio of dye to protein of 50:1. The reaction is stirred for 2 hours at room temperature. Sodium cyanoborohydride is added to a final concentration of 10 mM and the reaction is stirred for 4 hours at room temperature. The antibody conjugates are purified by dialysis and on MATREX GH 25 columns as described above. Antibodies that are oxidized for 1 hour typically yield a degree of substitution of 1 mole of dye per mole of IgG. Antibodies that are oxidized for 2 hours typically yield a degree of substitution of approximately 2 mole of dye per mole of IgG.

Example 49

Total Fluorescence of Selected Dye-Protein Conjugates as a Function of Degree of Substitution A series of goat anti-mouse IgG conjugates is prepared as in Example 47 so as to yield derivatives with similar degrees of substitution (DOS). The fluorescence emission spectra of a goat anti-mouse IgG conjugate of Compound 42 (DOS=1.2) and a goat anti-mouse IgG conjugate of CY-5 dye (DOS 2.5) at the same solution optical densities, excited at 600 nm, and in comparison to a solution of DDAO dye having the same absorbance used as a fluorescence standard. The conjugates of Compound 42 exhibit equal or greater fluorescence than the conjugates of CY-5 dye at similar degrees of substitution.

Example 50

Labeling β-Galactosidase with a Thiol-Reactive Dye

A solution of β-galactosidase, a protein rich in free thiol groups, is prepared in PBS (2.0 mg in 400 µL). The protein solution is then treated with a 20 mg/mL solution of Compound 43 in DMF. Unreacted dye is removed on a spin column. The degree of substitution by the dye is estimated using the extinction coefficient of the free dye. The protein concentration is estimated from the absorbance at 280 nm, corrected for the absorbance of Compound 43 at that wavelength.

Example 51

Fluorescence Energy Transfer in a Sulfonated-Rhodamine Conjugate of R-Phycoerythrin An R-phycoerythrin conjugate, prepared as in Example 47, is excited at 488 nm and the fluorescence emission is compared to that of unmodified R-phycoerythrin excited at the same wavelength. Highly efficient energy transfer occurs from the protein to the fluorescent dye. A conjugate of this complex with streptavidin is prepared essentially as described by Haugland (METH. MOL. BIOL. 45, 205 (1995), supra). This conjugate retains the energy transfer properties and is useful for cell staining in flow cytometers that utilize the argon-ion laser for excitation.

Example 52

Labeling and Use of a Wheat Germ Agglutinin Dye-Conjugate

Wheat germ agglutinin (100 mg, EY Laboratories) is dissolved in 5 mL NaHCO$_3$, pH 8.3, containing 9 mg N-acetylglucosamine. To this is added 9 mg of Compound 42. After 1 hour the solution is purified by gel filtration. A degree of substitution of 2-3 dyes per molecule is determined from the absorption at 633 nm.

A 1 mg/mL stock solution of the resulting wheat germ agglutinin (WGA) conjugate (Compound 42) is prepared in 0.1 M sodium bicarbonate ~pH 8. *Staphylococcus aureus* are cultured for 17 hours at 30° C. in TSB broth. Equal volumes of the TSB culture and a BSA solution (0.25% BSA+0.85% NaCl sterile filtered through 0.2 μM filter) are incubated at room temperature for 15 minutes. The BSA-bacterial suspension (200 μL) is centrifuged for 2 minutes at 350×g, capturing the bacteria on a filter membrane. The cells are resuspended in 90 μL of BSA solution and 10 μL of stain is added for 15 minutes. Following centrifugation, the bacteria are resuspended in BSA solution, and an aliquot is trapped between a slide and a glass coverslip.

The bacteria are observed on a Nikon Diaphot epi-fluorescence microscope using a fluorescein band pass filter set. Images are acquired using the Star-1 cooled CCD camera and the software package supplied with the camera is used for data analysis. Two images are collected for each stain, each image having a 2 sec. exposure time. When used according to Sizemore et al. (U.S. Pat. No. 5,137,810) the conjugate can distinguish between Gram positive and Gram negative bacteria.

Example 53

Simultaneous Labeling of Actin and Tubulin in Cultured Mammalian Cells

Bovine pulmonary artery cells (BPAEC) are grown to 30-50% confluence on glass. The cells are fixed with 3.7% formaldehyde, permeabilized with 0.2% Triton X-100, and blocked with 6% bovine serum albumin (BSA). All cells are incubated with mouse monoclonal anti-α-tubulin for 60 min.

A cell sample is labeled with a monoclonal mouse anti-tubulin (Molecular Probes, Inc.) and a goat anti-mouse IgG conjugate of ALEXA FLUOR 488 (Molecular Probes, Inc., Eugene, Oreg.) for 30 min, washed, and then incubated with the phalloidin dye-conjugate of Example 43 for an additional 30 min. The cells are rinsed with blocking buffer and mounted in phosphate-buffered saline (PBS) pH 7.4. The stained cells display microtubules decorated with green fluorescence and actin filaments decorated with red fluorescence.

Example 54

Utility of Protein Dye-Conjugates as Immunoreagents and Resistance to Photobleaching Goat anti-Mouse IgG conjugates of Compound 42 are prepared with degrees of substitution of approximately 2-4 (as in Example 47). CY5-labelled goat anti-mouse IgG is purchased from Jackson Immunoresearch. HEp-2 cell slides from INOVA (San Diego, Calif.) are hydrated in 1% bovine serum albumin (BSA) in PBS for 30 minutes. The slide is drained, human anti-nuclear antibody is applied, the slide is incubated 30 min and rinsed in PBS. Mouse anti-human antibody is applied, the slide is incubated 30 min and rinsed in PBS. The fluorescent anti-mouse antibody conjugate of choice is applied as a 5 μg/mL solution, diluted in 1% BSA/PBS. After 30 minutes the slides are rinsed in PBS, then in 50 mM Tris pH 8.0, mounted in 50 mM Tris pH 8.0, and viewed through an appropriate filter. All samples give predominantly nuclear staining. Quantitative intensity measurements permit comparison of dyes. Similar results are obtained using a biotinylated anti-mouse preparation and fluorescent streptavidin conjugates.

Figure 2:
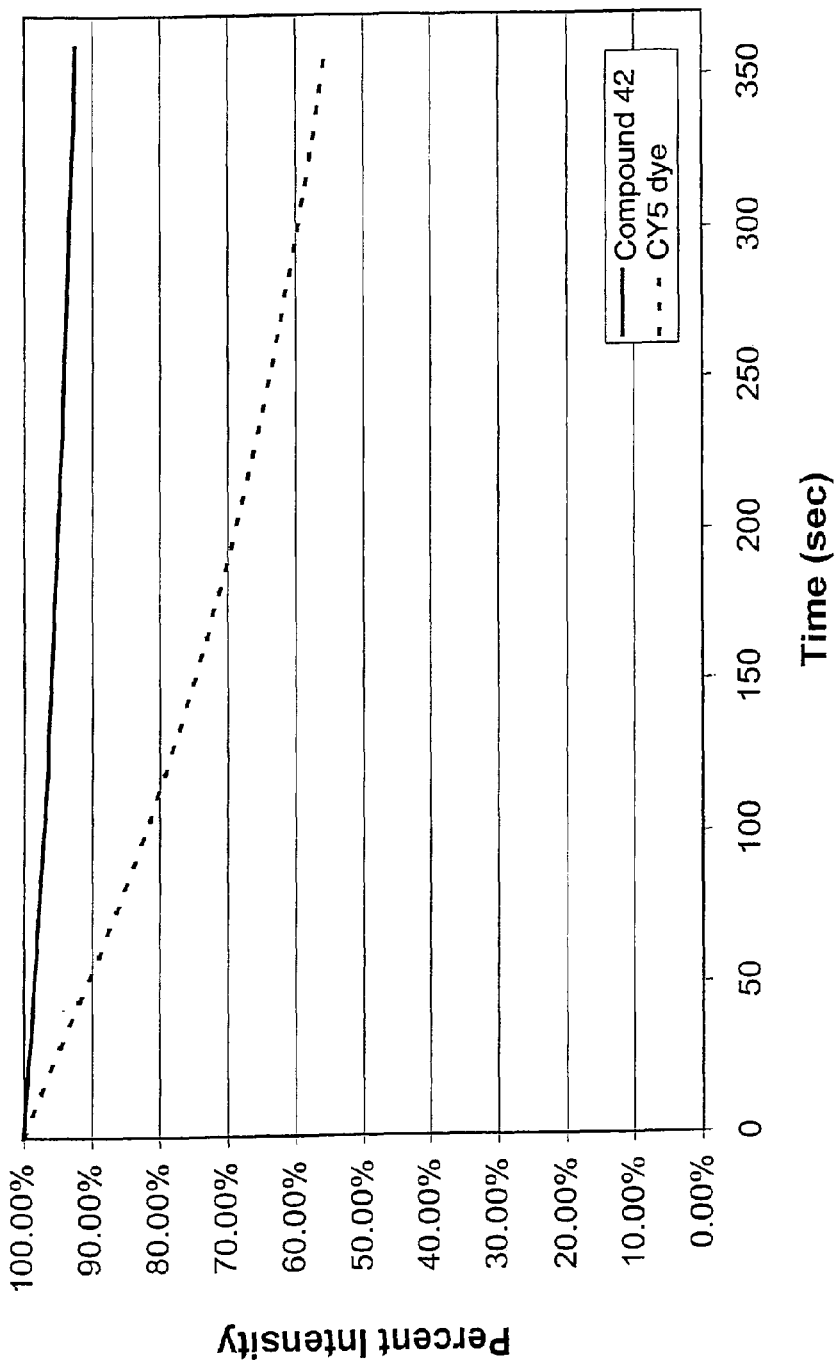
FIG. 2: A comparison of the rate of photobleaching between Compound 42 and the fluorescent dye CY-5 in phosphate-buffered saline, as described in Example 54.

For photobleaching measurements, one image of the slide is acquired every 5 seconds for 100 seconds with continuous illumination. Three fields of cells are bleached, and the photobleaching values are normalized and averaged. The antibody conjugates of Compound 42 are significantly more photostable than those of CY-5 dye (FIG. 2).

Example 55

Preparation and Use of a Fluorescent α-Bungarotoxin Dye-Conjugate

α-Bungarotoxin (1 mg) in 25 μL 0.1 M NaHCO$_3$ is treated with 1.5 equivalents of Compound 42 at room temperature for 2 hours. The product is purified by size exclusion, by ion exchange chromatography, and finally by reverse phase HPLC. Staining of acetylcholine receptors and detection of their resulting fluorescence is comparable to that obtained with TEXAS RED dye-conjugated α-bungarotoxin.

Example 56

Preparation of Aminodextran Dye-Conjugates 70,000 MW aminodextran (50 mg) derivatized with an average of 13 amino groups, is dissolved at 10 mg/mL in 0.1 M NaHCO$_3$. Compound 46 is added so as to give dye/dextran ratio of ~12. After 6 hours the conjugate is purified on SEPHADEX G-50, eluting with water. Typically 4-6 moles of dye are conjugated to 70,000 g dextran.

Example 57

Preparation of Fluorescent-Dye Labeled Microspheres

Uniform microspheres are conjugated to the dyes of the invention by one of five methods. In Method A, 1.0 μm amine-derivatized polystyrene microspheres are suspended at ~2% solids in 100 mM NaHCO$_3$, pH 8.3 and treated with 2 mg/mL of an amine-reactive dye. After 1 hour the microspheres are centrifuged and washed with buffer.

In Method B, carboxylate-modified microspheres are suspended in a solution of a protein that has been conjugated to a dye of the invention. The protein is passively adsorbed on the microspheres, and excess protein is removed by centrifugation and washing. Microparticles of a size that cannot be centrifuged are separated from excess protein by dialysis through a semi-permeable membrane with a high MW cutoff or by gel filtration chromatography.

In Method C the protein is covalently coupled through its amine residues to the carboxylate groups of the polymer using ethyl 3-(dimethylaminopropyl)carbodiimide (EDAC).

In Method D, biotinylated microspheres are treated with a streptavidin, avidin or anti-biotin conjugate of a dye of the invention, and the conjugates are isolated as in Method B.

In Method E, the microparticle is placed in a nonpolar solution of the desired dye. The microparticle swells in the presence of the organic solvent, and the dye is able to permeate the interior of the microparticle. Upon removing the solvent, the microparticle returns to its normal size, trapping the dye within the microparticle For example, to a stirred 100 mL suspension of carboxyate-modified latex (Interfacial Dynamics Corp., Portland, Oreg.) that is 4.2% solids is added 50 mL methanol. A dye solution is prepared that is 25-50 mg desired dye(s), 7.5 mL methylene chloride and 17.5 mL ethanol. The dye solution is added to the latex suspension at a low flow rate (~6 mL/hr), with stirring, using a syringe pump fitted with a Teflon delivery tube. After addition is complete, the organic solvents are removed under reduced pressure, and the aqueous suspension of dyed latex is filtered through glass wool to remove any additional debris. The microparticles are dialyzed in E-pure water (25 mm tubing, MW cutoff 12,000-14,000) until no more free dye is removed from the particles. The fluorescent latex suspension is filtered again through glass wool and then sonicated in a bath sonicator for 5 minutes to ensure monodispersity.

The larger particles can be analyzed for uniformity of staining and brightness using flow cytometry. The microspheres can be further coupled to proteins, oligonucleotides, haptens and other biomolecules for assays using methods well know in the art.

Example 58

Preparation of Fluorescent Liposomes Using the Dyes of the Invention

Selected dyes of the invention are sufficiently water soluble to be incorporated into the interior of liposomes by methods well known in the art (J. BIOL. CHEM. 257, 13892 (1982) and PROC. NATL. ACAD. SCI. USA 75, 4194 (1978)). Alternatively, liposomes containing dyes of the invention having a lipophilic substituent (e.g. alkyl having 11-22 carbons), within their membranes are prepared by co-dissolving the fluorescent lipid and the unlabeled phospholipid(s) that make up the liposome before forming the liposome dispersion essentially as described by Szoka, Jr. et al. (ANN. REV. BIOPHYS. BIOENG. 9, 467 (1980)).

Example 59

Preparation of Fluorescent Dye-Conjugates of Bacteria

Heat-killed *Escherichia coli* are suspended at 10 mg/mL in pH 8-9 buffer then incubated with 0.5-1.0 mg/mL of an amine-reactive dye, such as Compound 42. After 30-60 minutes the labeled bacteria are centrifuged and washed several times with buffer to remove any unconjugated dye. Labeled bacteria that are opsonized are taken up by macrophage, as determined by flow cytometry.

Example 60

Preparation of a Nucleotide Dye-Conjugate

To 2 mg of 5-(3-aminoallyl)-2'-deoxyuridine 5'-triphosphate (Sigma Chemical) in 100 μL water is added Compound 42 in 100 μL DMF and 5 μL triethylamine. After 3 hours, the solution is evaporated and the residue is purified by HPLC. The product fractions are lyophilized to give the red fluorescent nucleotide conjugate.

Alternatively fluorescent dye-conjugates of deoxyuridine 5-triphosphate are prepared from 5-(3-amino-1-propynyl)-2'-deoxyuridine 5'-triphosphate (as described in Hobbs, Jr. et al, supra).

Example 61

Preparation of an Oligonucleotide Dye-Conjugate

A 5'-amine-modified, 18-base M13 primer sequence (~100 μg) is dissolved in 4 μL 10 mM Tris-HCl, pH 8, 1 mM EDTA. To this is added 250 μg of Compound 42 in 100 μL 0.1 M sodium borate, pH 8.5. After 16 hours, 10 μL of 5 M NaCl and 3 volumes of cold ethanol are added. The mixture is cooled to −20° C., centrifuged, the supernatant is decanted, the pellet is rinsed with ethanol and then dissolved in 100 μL H$_2$O. The labeled oligonucleotide is purified by HPLC on a 300A C8 reverse-phase column using a ramp gradient of 0.1 M triethylammonium acetate (pH ~7) and acetonitrile (5→95% over 30 min). The desired peak is collected and evaporated to give the fluorescent oligonucleotide.

Example 62

Preparing DNA Hybridization Probes Using Fluorescent Nucleotide Dye-Conjugates For each labeling reaction, a microfuge tube containing about 1 μg of a ~700 bp Hind III-Bgl II fragment of the *E. coli* lacZ structural gene is heated for ~10 minutes at 95 C to fully separate the strands. The DNA is cooled on ice. A 2 μL of a 2 mg/mL mixture of random sequence hexanucleotides in 0.5 M Tris-HCl, pH 7.2, 0.1 M MgCl$_2$, 1 mM dithiothreitol is added, followed by 2 μL of a dNTP labeling mixture (1 mM dATP, 1 mM dGTP, 1 mM dCTP, 0.65 mM dTTP and 0.35 mM fluorescent-labeled dUTP (as prepared in Example 60). Sterile distilled, deionized water is added to bring the total volume to 19 L. 1 μL Klenow DNA polymerase (2 units/μL) is added. The samples are incubated 1 hr at 37° C. The reactions are stopped with 2 μL of 0.2 M EDTA, pH 8.0. The labeled DNA is precipitated with 2.5 μL of 4 M LiCl and 75

µL of −20° C. ethanol. After 2 hours at −20° C. the precipitated nucleic acids are centrifuged at 12,000 rpm. The pellets are washed with cold 70% ethanol, then cold 100% ethanol. The pellets are dried and dissolved in 10 mM Tris-HCl, pH 8.0, 1 mM EDTA. A portion of each sample is analyzed by gel electrophoresis on a 1% agarose minigel under standard conditions. The labeled DNA products are suitable for in situ hybridization experiments for the detection of RNA or DNA, such as is associated with the *E. coli* lacZ gene in cells or tissues.

Example 63

Incorporation of Fluorescent Nucleotide Conjugates into DNA Amplification Products A DNA amplification reaction is prepared as follows: 1 µL each of 20 µM solutions of two oligonucleotide primers that hybridize to the human-actin gene are added to a labeling reaction containing 5 µL DNA template (100 µmol of a plasmid containing the entire gene), 5 µL 10× reaction buffer (100 mM Tris, pH 8.3, 500 mM KCl), 2.5 µL 1 mM fluorescent-labeled dUTP (as prepared in Example 60), 1 µL 10 mM dATP, 1 µL 10 mM dCTP, 1 µL 10 mM dGTP, 1.5 µL 5 mM dTTP, 3 µL 25 mM $MgCl_2$, and 28 µL distilled, deionized water. The sample is transferred to a thermocycler and processed as follows: one cycle, 94° C., 2.5 minutes; 30 cycles, 94° C., 1 minute, 50° C., 1 minute, 72° C., 1 minute; one cycle, 72° C., 5 minutes; then 4° C. overnight. An aliquot of the sample is mixed with an equal volume of 10% glycerol, loaded onto a 0.9% agarose minigel and electrophoresed. Fluorescent bands of the expected size are visible when the gel is illuminated with 300-nm ultraviolet light.

Example 64

In Situ Hybridization of an RNA Probe

Mouse fibroblasts are fixed and prepared for mRNA in situ hybridization using standard procedures. A dye-labeled RNA probe is prepared by in vitro transcription of a plasmid containing the mouse actin structural gene cloned downstream of a phage T3 RNA polymerase promoter. Labeling reactions consist of combining 2 µL DNA template (1 µg DNA), 1 µL each of 10 mM ATP, CTP and GTP, 0.75 µL 10 mM UTP, 2.5 µL 1 mM fluorescent-labeled UTP, 2 µL 10× transcription buffer (400 mM Tris, pH 8.0, 100 mM $MgCl_2$, 20 mM spermidine, 100 mM NaCl), 1 µL T3 RNA polymerase (40 units/µL), 1 µL 2 mg/mL BSA, and 8.75 µL water. Reactions are incubated at 37° C. for two hours.

The DNA template is removed by treatment with 20 units DNase I for 15 minutes, at 37° C. The RNA transcript is purified by extraction with an equal volume of phenol:chloroform, 1:1, then by chromatography on SEPHADEX G50. Labeled RNA is denatured for 5 minutes at 50° C., then hybridized to cellular preparations using standard procedures. When preparations are washed and viewed through an appropriate filter set on a fluorescence microscope (excitation 610±10 nm; emission 670±20 nm), cells expressing actin mRNA show bright red fluorescence.

Example 65

Preparing DNA Hybridization Probes Using Fluorescent Platinum Dye-Compounds

A fluorescent platinum complex is prepared from a compound of the invention by adapting the methods provided in U.S. Pat. No. 5,714,327. For each labeling reaction, a microfuge tube containing 1 µg of pUC1.77 plasmid DNA containing a chromosome 1 human α-satellite probe (DNase treated to a fragment size between 500-1000 bp) in 5 mM Tris, pH 8, 1 mM EDTA, is heated for ~10 minutes at 95° C. to fully denature the DNA. The DNA is cooled on ice. 1 µL of a 1 mg/mL solution of the prepared platinum complex is added, followed by the addition of 5 mM Tris, pH 8, 1 mM EDTA to bring the total volume to 25 µL. The samples are incubated 15 minutes at 80° C. The reactions are stopped on ice. The labeled DNA is purified on a Bio-Rad Micro Bio-Spin P-30 Tris Chromatography Column. The labeled DNA products are suitable for in situ hybridization experiments.

Example 66

Preparing DNA Hybridization Probes Using Amine-Modified DNA an Amine-Reactive Dye of the Invention Nick translation is performed using pUC1.77 plasmid DNA containing a chromosome 1 human α-satellite probe. To a microcentrifuge tube is added, in the following order: 23.5 µL $H_2O$, 5 µL 10× Nick Translation buffer (0.5 M Tris-HCL, 50 mM $MgCl_2$, 0.5 mg/ml BSA, pH 7.8), 5 µL 0.1 M DTT, 4 µL d(GAC)TP mix (0.5 mM dATP, 0.5 mM dCTP, 0.5 mM dGTP), 1 µL 0.5 mM dTTP, 4 µL 0.5 mM aminoallyl-dUTP, 1 µL 1 µg/µL template DNA, 5 µL DNase I (1 µg/mL, 2000 Kunitz units/mg), 1.5 µL DNA polymerase I (10 U/µL). The tube is incubated 2 hours at 15° C., then brought to a final volume of 100 µL with $H_2O$. The amine-modified DNA is purified using a QIAQUICK PCR purification Kit (Qiagen) with the following modifications to purify the DNA from the enzyme and amine-containing compounds: 75% EtOH is substituted for the wash buffer, $H_2O$ is substituted for the elution buffer, and elution is performed twice for 5 minutes each. The DNA is precipitated by adding 1/10 volume 3M sodium acetate and 2.5 volumes 100% EtOH, incubated at −70° C. for 30 minutes, centrifuged for 15 minutes, and washed with 70% EtOH.

The amine-modified DNA is resuspended in 5 µL $H_2O$. To the solution is added 3 µL 25 mg/ml sodium bicarbonate and 50 µg Compound 42 in 5 µL DMF. The reaction is incubated for 1 hour at room temperature in the dark. 90 µL $H_2O$ is added to the reaction and it is purified using a QIAQUICK PCR purification kit (QIAGEN), with the following modifications: three washes are performed with 75% EtOH and three elutions of 5 minutes each with the QIAGEN elution buffer. The DNA is precipitated as before. The labeled DNA products are suitable for in situ hybridization experiments.

Example 67

Discrimination of Live and Dead Cells Using the Dyes of the Invention

Selected dyes of the invention are highly polar, and therefore relatively impermeable to the membranes of live cells. These dyes can therefore be used to discriminate cells that have intact versus compromised cell membranes in a single-color assay as follows:

Mouse monocyte-macrophage, Abelson Leukemia Virus Transformed (RAW264.7) cells are trypsinized and washed with phosphate buffered saline (PBS), pH 7.2. Approximately 8-10 million cells suspended in 180 µL of PBS, pH 7.2 are placed in a glass test tube and heated in a water bath at 50° C. for 20 minutes to kill a fraction of the cells. Approximately 60

μL (2-3 million cells) of the cell suspension is added to 940 μL of PBS, pH 7.2, followed by 0.1 μL of a 1 mg/mL solution of Compound 42 in DMSO. The mixture is incubated on ice for 30 minutes and washed twice with PBS, followed by addition of 200 μL of PBS, pH 7.2. An identical aliquot of cells is treated with 2 μL of a 150 μM solution of propidium iodide in water (as a control for dead cells). Analysis of the cell suspension using flow cytometry shows that populations of dead cells stained by Compound 42 and those stained by propidium iodide are very similar.

Example 68

Neuronal Tracing Using a Hydrazide-Labeled Fluorophore

Neurons from zebrafish embryos are microinjected with Compound 44, using standard methods as described by Blankenfeld et al. (J. NEUROSCI. METH. 36, 309 (1991)). The neurons rapidly fill with the dye throughout their volume and their red fluorescence is readily observable. The staining is fixable in the cells using formaldehyde and standard fixing methods.

Example 69

Preparation of Compound 65

Compound 10 (0.15 g, 0.51 mmol), 1-(2-bis(methoxycarbonylmethyl)amino-5-fluoro)-2-(2-bis(methoxycarbonylmethyl)amino-5-formylphenoxy)ethane (0.15 g, 0.25 mmol), and catalytic p-TsOH are suspended in propionic acid (10 mL) under an argon atmosphere and sparged with argon for 40 minutes while being heated to 60° C. The reaction mixture is stirred for 3 hours, then cooled. The solution is poured into a solution of 3M sodium acetate (100 mL) with stirring. The resulting precipitate is collected by suction filtration, rinsed with water, and dried in vacuo to give a dihydro intermediate as pale green powder.

The dihydro intermediate (0.25 mmol) is dissolved in methanol/chloroform (1:1, 12 mL) and treated with p-chloranil (0.123 g, 0.50 mmol). The resulting mixture is stirred at room temperature until TLC analysis shows consumption of starting material (approximately 1.5 hours). The reaction mixture is suction filtered and the filtrate concentrated in vacuo. The resulting dark blue residue is purified by flash chromatography on 35 g silica gel using chloroform:methanol:acetic acid (50:5:1) as eluant. Pure product fractions are combined and concentrated in vacuo to give the oxidized intermediate as a dark blue solid.

The blue oxidized intermediate (0.04 mmol) is converted to the free carboxylic acid form by treatment with 1 M KOH (0.35 mL, 0.35 mmol) in dioxane/methanol (1:1, 5 mL). The resulting dark amber mixture is stirred at room temperature overnight, then concentrated in vacuo. The residue is suspended in 5 mL water, and the pH (13) is adjusted to 2 by the addition of aqueous HCl. The resulting blue precipitate is collected by filtration, rinsed with water, and dried under vacuum to yield a dark blue powder. The product is further purified by dissolution in dilute aqueous KOH solution, followed by chromatography on SEPHADEX LH-20 resin using water as eluant. Pure product fractions are combined and lyophilized to give Compound 65 as a dark blue powder, $R_f$=0.45 (dioxane:isopropyl alcohol:water:ammonium hydroxide 15:58:13:13)).

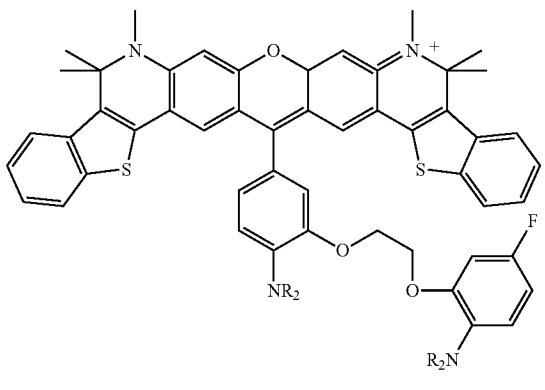

Compound 65

R = CH$_2$CO$_2$K

Example 70

Preparation of Compound 66

Compound 10 (0.15 g, 0.51 mmol), N,N,N',N'-tetramethoxycarbonylmethyl-2'-amino-4'-diphenylmethoxycarbonylphenoxy)-2-(2"-aminophenoxy)ethane (0.25 mmol), and catalytic p-TsOH are suspended in propionic acid (10 mL) under an argon atmosphere and sparged with argon for 40 minutes while being heated to 70° C. The reaction mixture is stirred for 20 hours, then cooled. The solution is poured into a solution of 3M sodium acetate (100 mL) with stirring. The resulting precipitate is collected by suction filtration, rinsed with water, and dried in vacuo to give a dihydro intermediate 4-benzhydryl ester as pale green powder.

The dihydro intermediate (0.25 mmol) is dissolved in methanol/chloroform (1:1, 12 mL) and treated with p-chloranil (0.123 g, 0.50 mmol). The resulting mixture is stirred at room temperature until TLC analysis shows consumption of starting material (approximately 1.5 hours). The reaction mixture is suction filtered and the filtrate concentrated in vacuo. The resulting dark blue residue is purified by flash chromatography on 35 g silica gel using chloroform:methanol:acetic acid (50:5:1) as eluant. Pure product fractions are combined and concentrated in vacuo to give the oxidized intermediate benzhydryl ester as a dark blue solid.

The oxidized intermediate benzhydryl ester (0.15 mmol) is treated with 1:1 chloroform/trifluoroacetic acid (10 mL) for one hour, then concentrated in vacuo. Chloroform (2×10 mL) is evaporated from the residue, which is triturated with ether (20 ml). The resulting oxidized intermediate 4-carboxylic acid is collected by suction filtration as a blue powder.

The oxidized intermediate carboxylic acid (0.10 mmol) in DMF (2 mL) is treated with diisopropylethylamine (DIEA, 0.35 mL, 2 mmol) and dry trifluoroacetyl-N-hydroxysuccinimide (TFA-SE, 225 mg, 1 mmol). The resulting blue mixture is stirred for 2 h, then more TFA-SE (113 mg, 0.5 mmol) is introduced and the mixture stirred for another 16 h. The mixture is diluted with CHCl$_3$ (50 mL), washed with 1% AcOH (3×20 mL), H$_2$O (25 mL), sat. NaCl (50 mL), filtered and evaporated. Ether (25 mL) is added to the residue, and the precipitated product filtered and washed with ether to give the oxidized intermediate 4-succinimidyl ester as a dark blue solid.

To a solution of 4-aminomethylbenzophenone (0.080 mmol) in DMF (1 mL) and DIEA (0.055 mL, 0.40 mmol) is added a solution of the oxidized intermediate 4-succinimidyl ester (0.040 mmol) in 1 mL DMF. The resulting mixture is stirred under subdued light for 3 h, diluted with CHCl$_3$ (200 mL), washed with 1% AcOH (3×150 mL), H$_2$O (100 mL), sat. NaCl (200 mL), filtered and evaporated. The residue is purified on two preparative TLC SiO$_2$ plates, using 12% MeOH and 2.5% AcOH in CHCl$_3$ as eluent to give the photoactivatable tetramethyl ester intermediate as a dark blue solid.

To a solution of the photoactivatable tetramethyl ester intermediate (0.025 mmol) in MeOH (2 mL) and H$_2$O (1 mL) is added 1N KOH to give pH 12.0. The mixture is stirred under subdued light for 20 h, then pH-adjusted to 8.5 with 0.1 N HCl. The mixture is evaporated and the residue purified on a Sephadex LH-20 column (1.6×40 cm bed) using H$_2$O as eluant. Pure product fractions are pooled and lyophilized to give photoactivatable Compound 66 as a fluffy dark blue powder.

Compound 66

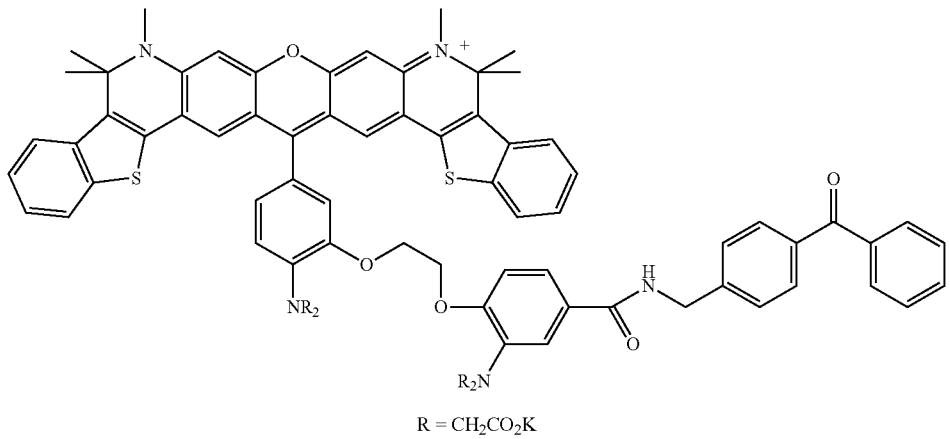

R = CH$_2$CO$_2$K

We claim:
1. A compound of the formula:

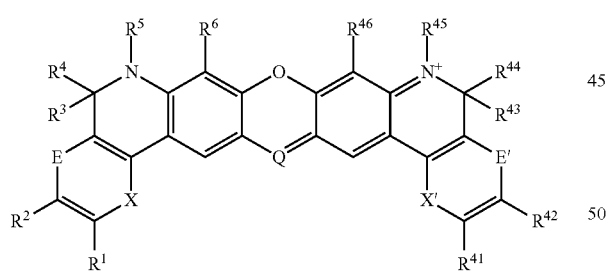

wherein
R$^1$ and R$^{41}$ are independently hydrogen or sulfonic acid;
R$^2$ and R$^{42}$ are independently selected from the group consisting of hydrogen, cyano, halogen, carboxylic acid, sulfonic acid, C$_1$-C$_6$ alkyl or alkoxy, aryl, heteroaryl, -L-R, and -L-S$_c$, wherein said alkyl or alkoxy is optionally substituted by carboxylic acid, sulfonic acid, or halogen and said aryl or heteroaryl is optionally substituted one or more times by C$_1$-C$_6$ alkyl, C$_1$-C$_6$ perfluoroalkyl, cyano, halogen, azido, carboxylic acid, sulfonic acid, or halomethyl;
R$^3$, R$^4$, R$^{43}$, and R$^{44}$ are each methyl;
R$^5$ and R$^{45}$ are independently selected from the group consisting of hydrogen, methyl, carboxymethyl, C$_1$-C$_6$ alkyl, aryl, heteroaryl, -L-R$_x$ and -L-S$_c$, wherein said alkyl is optionally substituted by carboxylic acid, sulfonic acid, amino, or halogen and said aryl or heteroaryl is optionally substituted one or more times by C$_1$-C$_6$ alkyl, C$_1$-C$_6$ perfluoroalkyl, cyano, halogen, carboxylic acid, sulfonic acid, or halomethyl;

R$^6$ and R$^{46}$ are both hydrogen;

one of E and X is O, S, or NR$^8$; the other is absent; and one of E' and X' is O, S, or NR$^8$; the other is absent;

wherein R$^8$ is independently selected from the group consisting of hydrogen, methyl, carboxymethyl, C$_2$-C$_6$ alkyl, -L-R$_x$ and -L-S$_c$ wherein said alkyl is optionally substituted by carboxylic acid, sulfonic acid, amino, or halogen; and Q is CR$^{28}$, wherein R$^{28}$ is of the formula

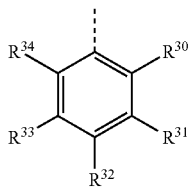

wherein R$^{30}$, R$^{31}$, R$^{32}$, R$^{33}$, and R$^{34}$ are independently selected from the group consisting of hydrogen, F, Cl, Br, I, sulfonic acid, carboxylic acid, CN, nitro, hydroxy, azido, amino, hydrazino, C$_1$-C$_{18}$ alkyl, C$_1$-C$_{18}$ alkoxy, C$_1$-C$_{18}$ alkylthio, C$_1$-C$_{18}$ alkanoylamino, C$_1$-C$_{18}$ alkylaminocarbonyl, C$_2$-C$_{36}$ dialkylaminocarbonyl, C$_1$-C$_{18}$ alkyloxycarbonyl, C$_7$-C$_{18}$ arylcarboxamido, -L-R$_x$ and -L-S$_c$, wherein said alkyl or aryl portions of said R$^{30}$, R$^{31}$, R$^{32}$, R$^{33}$, and R$^{34}$ are optionally substituted one or more times by substituents selected from the group consisting of F, Cl, Br, I, hydroxy, carboxylic acid, a carboxylic acid ester of a C$_1$-C$_6$ alcohol, amino, C$_1$-C$_6$ alkylamino, C$_1$-C$_6$ dialkylamino and C$_1$-C$_6$ alkoxy; or a pair of adjacent R$^{31}$, R$^{32}$, R$^{33}$, and R$^{34}$ substituents, when taken in combination, form a fused 6-membered aromatic ring that is optionally further substituted by carboxylic acid; and wherein L is a covalent linkage;
$R_x$ is a reactive group; and
$S_c$ is a conjugated substance.

2. The compound according to claim 1, wherein said L is independently a single covalent bond or a covalent linkage having 1-20 nonhydrogen atoms selected from the group consisting of C, N, O, P, and S.

3. The compound according to claim 1, wherein said $R_x$ is independently selected from the group consisting of an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine, an imido ester, an isocyanate, an isothiocyanate, a maleimide, a phosphoramidite, a reactive platinum complex, a sulfonyl halide, and a thiol group.

4. The compound according to claim 1, wherein said $S_c$ is independently selected from the group consisting of an amino acid, a peptide, a protein, a tyramine, a carbohydrate, a metal chelating moiety, a nucleoside, a nucleotide, an oligonucleotide, a nucleic acid, a hapten, a psoralen, a drug, a hormone, a lipid, a lipid assembly, a polymer, a polymeric microparticle, a biological cell, and a virus.

5. The compound according to claim 1, wherein one of $R^{30}$, $R^{31}$, $R^{32}$, $R^{33}$, and $R^{34}$ is $-L-R_x$ or $-L-S_c$.

6. The compound according to claim 1, of the formula:

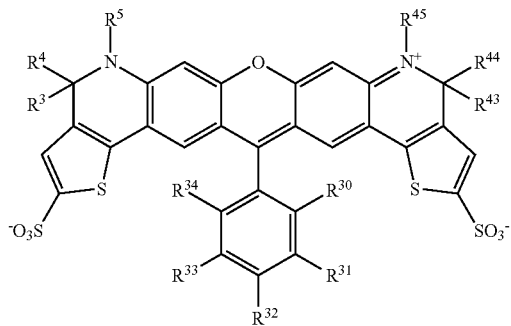

wherein
$R^5$ and $R^{45}$ are independently methyl or ethyl;
$R^{30}$ is sulfonic acid or carboxylic acid;
$R^{31}$ and $R^{34}$ are independently hydrogen, F, or Cl; one of $R^{32}$ and $R^{33}$ is H, F, or Cl, and the other of $R^{32}$ and $R^{33}$ is $-L-R_x$ or $-L-S_c$, wherein L is a covalent linkage of the formula $-S(CH_2)_a COO(CH_2)_b-$ or the formula $S(CH_2)_a CONH(CH_2)_b-$, wherein a is an integer between 0 and 10, and b is an integer between 0 and 10 provided that a and b are not both 0;

wherein $R_x$, where present, is a carboxylic acid, an activated ester of a carboxylic acid, a haloacetamide, a hydrazine, an isothiocyanate, a maleimide group, or a reactive platinum complex; and wherein $S_c$, where present, is an amino acid, a peptide, a protein, an ion-complexing moiety, a nucleoside, a nucleotide, an oligonucleotide, lectin or a nucleic acid.

7. The compound according to claim 6, wherein $R_x$, is independently a maleimide group or a succinimidyl ester of a carboxylic acid.

8. The compound according to claim 6, wherein $S_c$ is independently an antibody or antibody fragment or a BAPTA or APTRA ion-complexing moiety.

9. A method of staining a biological sample, comprising:
combining a dye solution comprising a compound of the formula as described in claim 1 with a biological sample in a concentration sufficient to yield a detectable optical response under desired conditions.

10. The method according to claim 9, further comprising:
combining the sample with a detection reagent that has spectral properties that are detectably different from said optical response; and/or
determining a characteristic of the sample by comparing the optical response with a standard response parameter;
wherein the sample is immobilized in or on a solid or semi-solid matrix that is a membrane, an electrophoretic gel, a silicon chip, a microwell plate, or a microfluidic chip.

11. The method according to claim 9, wherein the sample comprises cells; and/or further comprising tracing a temporal or spatial location of the optical response with the sample.

12. The method according to claim 9, wherein for said compound $S_c$ is an amino acid, a peptide, a protein, a polysaccharide, a nucleotide, a nucleoside, an oligonucleotide, a nucleic acid polymer, an ion-complexing moiety, a lipid, or a non-biological organic polymer or polymeric microparticle, wherein $S_c$ is optionally bound to one or more fluorophores that are the same or different.

13. The method according to claim 9, wherein for said compound, $S_c$ is an ion-complexing moiety that is a BAPTA or an APTRA.

* * * * *

UNITED STATES PATENT AND TRADEMARK OFFICE
CERTIFICATE OF CORRECTION

PATENT NO. : 8,183,375 B2  
APPLICATION NO. : 12/901713  
DATED : May 22, 2012  
INVENTOR(S) : Zhenjun Diwu, Jixiang Liu and Kyle Gee Page 1 of 1

It is certified that error appears in the above-identified patent and that said Letters Patent is hereby corrected as shown below:

At Claim 1, column 71, line 59, please delete "R" and substitute --$R_x$--, therefor.

At Claim 1, column 72, line 10, please delete "X is 0" and substitute --X is O--, therefor.

At Claim 7, column 74, line 14, please delete the "," after '$R_x$'.

Signed and Sealed this  
Eleventh Day of September, 2012

David J. Kappos  
*Director of the United States Patent and Trademark Office*